United States Patent
Kumar et al.

(10) Patent No.: US 9,828,447 B2
(45) Date of Patent: Nov. 28, 2017

(54) PROCESS FOR THE PREPARATION OF 2,2'-BIS-INDENYL BIPHENYL LIGANDS AND THEIR METALLOCENE COMPLEXES

(71) Applicants: SAUDI BASIC INDUSTRIES CORPORATION, Riyadh (SA); SABIC GLOBAL TECHNOLOGIES B.V., Bergen op Zoom (NL)

(72) Inventors: Mudubagilu Udaya Kumar, Baroda (IN); Paresh Bhagvanbhai Rasadiya, Baroda (IN); Bharatkumar Ravjibhai Paghadar, Baroda (IN); Sambhaji Nanasaheb Chougule, Baroda (IN)

(73) Assignees: SAUDI BASIC INDUSTRIES CORPORATION, Riyadh (SA); SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 14/911,562

(22) PCT Filed: Aug. 19, 2014

(86) PCT No.: PCT/EP2014/067665
§ 371 (c)(1),
(2) Date: Feb. 11, 2016

(87) PCT Pub. No.: WO2015/024938
PCT Pub. Date: Feb. 26, 2015

(65) Prior Publication Data
US 2016/0194414 A1 Jul. 7, 2016

(30) Foreign Application Priority Data

Aug. 20, 2013 (EP) ................................. 13181087
Aug. 20, 2013 (EP) ................................. 13181089
Aug. 20, 2013 (EP) ................................. 13181090

(51) Int. Cl.
| | | |
|---|---|---|
| *C08F 10/02* | (2006.01) | |
| *C09K 11/06* | (2006.01) | |
| *C07F 17/00* | (2006.01) | |
| *C08F 10/00* | (2006.01) | |
| *C07C 1/32* | (2006.01) | |
| *C07F 5/02* | (2006.01) | |
| *B01J 31/38* | (2006.01) | |

(52) U.S. Cl.
CPC ............. *C08F 10/02* (2013.01); *B01J 31/38* (2013.01); *C07C 1/321* (2013.01); *C07F 5/02* (2013.01); *C07F 5/025* (2013.01); *C07C 2521/18* (2013.01); *C07C 2523/44* (2013.01); *C07C 2531/24* (2013.01); *C07C 2602/08* (2017.05)

(58) Field of Classification Search
None
See application file for complete search history.

(56) References Cited

U.S. PATENT DOCUMENTS 6,342,622 B1   1/2002   Arts et al.

FOREIGN PATENT DOCUMENTS

| WO | 2007105657 A1 | 9/2007 |
| WO | 2008127004 A1 | 10/2008 |
| WO | 2013091836 A1 | 6/2013 |
| WO | 2013091837 A1 | 6/2013 |

OTHER PUBLICATIONS

Ijpeij, Edwin, G., et al, "A Suzuki Coupling Based Route to 2,2¢-Bis(2-indenyl)biphenyl Derivatives", J. Org. Chem. 2002, 67, 169-176.
International Search Report for PCT/EP2014/067665 dated Nov. 11, 2014, 5 pages.
Written Opinion of the International Searching Authority for PCT/EP2014/067665, dated Nov. 11, 2014, 5 pages.

*Primary Examiner* — Yun Qian
(74) *Attorney, Agent, or Firm* — Cantor Colburn LLP

(57) ABSTRACT

The invention relates to a novel process for the preparation of 2,2'-bis indenyl biphenyl ligands of following formula (3): The invention also relates to metallocene complexes prepared using the novel process for the preparation of 2,2-bis indenyl biphenyl ligands. The invention also relates to novel intermediates used in the process for the preparation of 2,2'-bis indenyl biphenyl ligands.

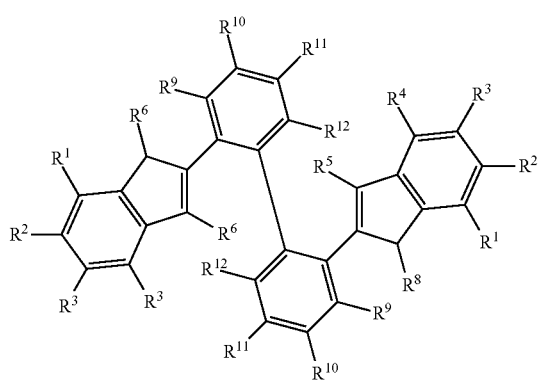

(3)

10 Claims, No Drawings

PROCESS FOR THE PREPARATION OF 2,2'-BIS-INDENYL BIPHENYL LIGANDS AND THEIR METALLOCENE COMPLEXES

This application is a national stage application of PCT/EP2014/067665 filed Aug. 19, 2014, which claims priority to European Applications EP13181090.5 filed Aug. 20, 2013, EP13181087.1 filed Aug. 20, 2013, and EP13181089.7 filed Aug. 20, 2013, which are hereby incorporated by reference in their entirety.

The present invention relates to a process for the preparation of 2,2'-bis(2-indenyl)biphenyl ligands and their metallocene complexes. The invention also relates to novel intermediates in said process and to the process of the preparation of said intermediates.

Metallocene complexes with 2,2'-bis(2-indenyl)biphenyls ligands have proven to be highly active in the polymerization of α-olefins, such as ethylene after activation with aluminoxane cocatalysts. However, the known syntheses of the ligands used in the synthesis of these metallocene complexes are tedious.

For instance, U.S. Pat. No. 6,342,622B1 describes a process for the preparation of indenyl ligands, which are prepared using diboronic acid, which is prepared via the di-lithio complex of biphenyl. This di-lithio complex is highly pyrophoric and it is difficult to produce at a large scale. Further, the yields of the preparation of this di-lithio produce are not consistent and undesired byproducts, such as mono isomer are formed. In addition, the purification of the di-lithio product is difficult and risky. Since pure di-lithio is required for diboronic acid preparation, multiple washings of hexane are needed, which leads to a lot of undesired organic waste, which is undesired from an environmental point of view.

Ijpeij, E et al. describes in the Journal of Organic Chemistry, 2002, Vol. 67, pages 169-176, a process for bis Suzuki coupling. This process however again relies on a preparation via a di-lithio complex of biphenyl, which is highly pyrophoric and makes the up scaling of the process extremely difficult. In addition, the process uses a homogeneous catalyst, such as Pd(PPh$_3$)$_4$, so that catalyst recovery can be difficult. Moreover, the bis-Grignard reaction described in this Journal of Organic Chemistry, 2002, Vol. 67, pages 169-176 and in Organometallics, 1993, Vol. 12, page 4391 requires very high dilution of the solvent (1:70) and is therefore also difficult to scale-up.

WO2013/091837A1 discloses a process comprising the step of reacting a 2-indenylpinacolyl borane compound with a bromosubstituted compound in the presence of a Pd catalyst and a base to form the corresponding bridged bis(indenyl) ligand. However, this process involves the use of the hazardous butyl lithium and requires a lot of energy. Also, the process is difficult to scale-up.

WO2013/091836A1 discloses a process comprising the step of (a) reacting a 2-indenylboranic acid (ester) with a bromosubstituted compound in the presence of the Pd catalyst bis(triphenylphosphin)palladium dichloride (PPh$_3$)$_2$PdCl$_2$) and a base to form the corresponding bridged bis(indenyl) ligand. However, this process involves the use of the hazardous butyl lithium and requires a lot of energy. Also, the process is difficult to scale-up.

It is the object of the invention to provide an improved process for the preparation of 2,2'-bis(2-indenyl)biphenyls ligands.

This object is achieved by a process comprising the step of
reacting a compound of formula (1)

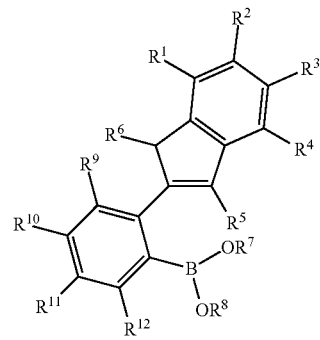

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group wherein $R^7$ and $R^8$ each independently stand for H, or an alkyl or aryl or wherein $R^7$ and $R^8$ may form a ring together with the oxygen atoms to which they are bound
and wherein $R^9$, $R^{10}$, $R^{11}$ and $R^{12}$ all stand for H with a compound of formula (2)

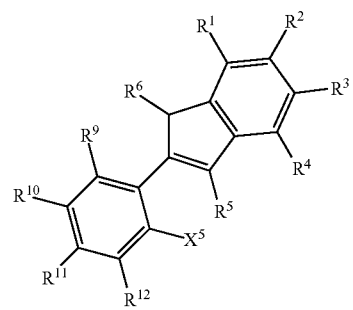

wherein $R^1$, $R^2$, $R^3$, $R^4$, $R^5$, $R^6$, $R^9$, $R^{10}$, $R^{11}$ and $R^{12}$ m are as defined herein and wherein $X^5$ stands for a halogen in a solvent in the presence of a Pd catalyst and a base
to form the corresponding compound of formula (3)

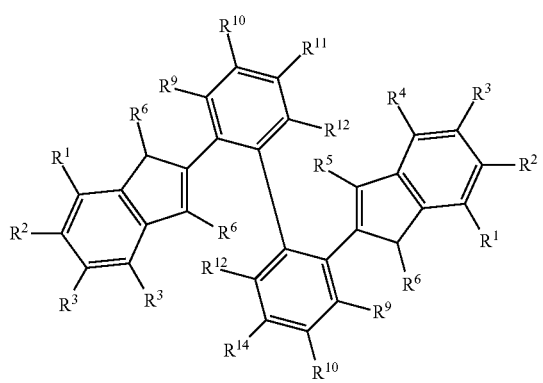

wherein $R^1$, $R^2$, $R^3$, $R^4$, $R^5$, $R^6$, $R^9$, $R^{10}$, $R^{11}$ and $R^{12}$ m are as defined herein.

The process of the invention is easily upscaleable, gives consistent yields and is easy to work-up. Additionally, less by-products are formed and the process is less hazardous.

$R^1$, $R^2$, $R^3$, $R^4$, $R^5$ and $R^6$ $R^1$, $R^2$, $R^3$, $R^4$, $R^5$ and $R^6$ may each independently stand for H, a hydrocarbon radical having 1-20 C-atoms, a halide, an alkoxy group having 1-6 C-atoms, an alkylsulphide, an amine, a Si or B containing group or a P-containing group, preferably for H, a hydrocarbon radical having 1-20 C-atoms or a halide. Examples of hydrocarbon radicals includes alkyl groups, for example methyl, ethyl, propyl, for example i-propyl or n-propyl; butyl, for example i-butyl or n-butyl; hexyl and decyl; aryl groups, for example phenyl, mesityl, tolyl and cumenyl; aralkyl groups for example benzyl, pentamethylbenzyl, xylyl, styryl and trityl and alkaryl groups. The hydrocarbon radical preferably has from 1-6 C-atoms and is most preferably methyl. Examples of halides include chloride, bromide and fluoride. Examples of alkoxy groups having 1-6 C-atoms include but are not limited to methoxy, ethoxy and phenoxy. Examples of alkylsulphides include methylsulphide, phenylsulphide and n-butylsulphide. Examples of amines include dimethylamine, n-butylamine. Examples of Si or B containing groups include trimethylsilicium ($Me_3Si$) and diethylboron ($Et_2B$). Examples of P-containing groups include dimethylphosphor ($Me_2P$) and diphenylphosphor ($Ph_2P$).

Preferably, $R^5$ and/or $R^6$ stand for H. More preferably, $R^1$ and/or $R^2$ and/or $R^3$ and/or $R^4$ and/or $R^5$ and/or $R^6$ stand for H. Most preferably $R^1$, $R^2$, $R^3$, $R^4$, $R^5$ and $R^6$ all stand for H.

$R^7$ and $R^8$ $R^7$ and $R^8$ each independently stand for H, or an alkyl, for example a cyclic or acylic alkyl, preferably a linear alkyl, such as i-propyl and/or for example an alkyl having 1 to 6 carbon atoms or aryl, for example phenyl or wherein $R^7$ and $R^8$ may form a ring together with the oxygen atoms to which they are bound, or for example $R^7$ and $R^8$ may form a pinacolyl ring or diamino ring together with the oxygen atoms to which they are bound. Preferably $R^7$ and $R^8$ stand for H or $R^7$ and $R^8$ form a pinacolyl ring together with the oxygen atoms to which they are bound.

$R^9$, $R^{10}$, $R^{11}$ and $R^{12}$ $R^9$, $R^{10}$, $R^{11}$ and $R^{12}$ all stand for H.

$X^5$ $X^5$ stands for halogen, preferably Cl, Br or F, more preferably for Br.

The process to form the compound of formula (3) as described above may in principle be performed in any solvent known to be suitable for Suzuki couplings, such as alcohols, for example methanol or ethanol; aromatic solvents, for example benzene, toluene or xylene; ethers, for example tetrahydrofuran, dioxane or dimethoxyethane; amides, for example dimethylformamide and water that is preferably substantially free of oxygen. Preferably organic solvents are used, more preferably aromatic solvents, for example toluene. Mixtures of solvents, such as the solvents mentioned herein may also be used, for example a mixture of water that is preferably substantially free of oxygen and an aromatic solvent or a mixture of water with an alcohol such as ethanol.

The Pd catalysts that can be used in the preparation of the compound of formula (3) are in principle all Pd catalysts known to be suitable for Suzuki couplings. Preferably, a Pd(0) catalyst or a catalyst wherein Pd(0) is generated in situ by reduction of (more stable) Pd(II) compounds is used. Examples of Pd catalysts include tetrakis(triphenylphosphin)palladium (($Ph_3P)_4Pd$), palladium (II) acetate (Pd($O_2CCH_3)_2$ or Pd(Oac)$_2$), tris(dibenzylideneacetone)dipalladium (PD(dba)$_2$), bis(triphenylphosphin)palladium dichloride (PPh$_3)_2$PdCl$_2$), 1,1'-bis(diphenylphosphino)ferrocene]dichloropalladium(II) (PdCl$_2$(dppf)), [1,2-bis(diphenylphosphino)ethane]dichloropalladium(II), (PdCl$_2$(dppe)), bis(tricyclohexyl phosphine)palladium(0), bis(triethylphosphine)palladium(II) chloride, bis(tri-t-butylphosphine)palladium(0), bis[1,2-bis(diphenylphosphino)ethane] palladium (0), bis[tri(o-tolyl)phosphine]palladium(II) chloride, trans-benzyl(chloro)bis(triphenylphosphine)palladium(II).

Preferably as Pd catalyst, tetrakis(triphenylphosphin)palladium (Pd(PPh$_3)_4$) or Pd on carbon (Pd/C) is used. Pd/C is thereby a heterogeneous catalysts and therefore very easy to recover and reuse.

The base that can be used in the preparation of the compound of formula (3) can in principle be any base, for example an inorganic or an organic base. Preferably an organic base is used in the preparation of the bridged bis-indenyl) ligand of formula (3), such as for example a quaternary ammonium salt, for example tetra n-butylammoniumacetate or tetra-butyl ammonium hydroxide or a tertiary amine, for example triethylamine (Et$_3$N). Other examples of suitable bases include but are not limited to sodium carbonate, sodium acetate, sodium tert-butoxide, potassium carbonate, potassium iodide, sodium iodide, potassium acetate, cesium carbonate, cesium fluoride, lithium hydroxide, sodium hydroxide, sodium ethoxide, potassium fluoride and potassium phosphate. Preferably, the base used in the reaction of the compound of formula (1) with the compound of formula (2) is tetra-butyl ammonium hydroxide.

In principle, the reaction conditions for the process to form the compound of formula (3) are not critical and the temperatures, pressures and reaction time known to be suitable for Suzuki couplings, may be used by the person skilled in the art and optimal conditions can be found using routine experimentation. For example, the temperature may be from 60 to 120° C., as at temperatures below 60° C., the reaction hardly proceeds and at temperatures of above 120° C., tarring may occur. Preferably, the temperature is chosen to be at least 60, preferably at least 75 and/or at most 100, preferably at most 85° C. The pressure under which the process is performed is preferably atmospheric pressure (1 bar). The reaction time may for example be in the range from 36 to 48 hours.

The compound of formula (1) and (2) are preferably reacted in a molar ratio of 1:1 to 1:4, preferably in a molar ratio of about 1:1.2.

In another embodiment, the invention also relates to the novel compound of formula (1)

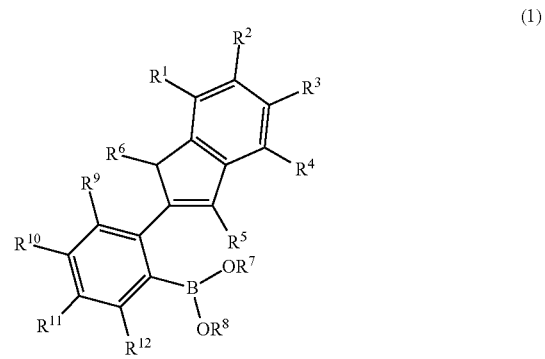

(1)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group
and
wherein $R^7$ and $R^8$ each independently stand for H, or an alkyl or aryl or wherein $R^7$ and $R^8$ may form a ring together with the oxygen atoms to which they are bound and wherein $R^9$, $R^{10}$, $R^{11}$ and $R^{12}$ all stand for H.

The compound of formula (1), wherein $R^7$ and $R^8$ each independently stand for H, or an alkyl or aryl may be prepared using the process of the invention, further comprising the step of preparing the compound of formula (1)

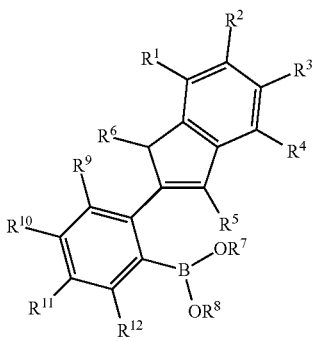
(1)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group
wherein $R^7$ and $R^8$ each independently stand for H, or an alkyl or aryl
and wherein $R^9$, $R^{10}$, $R^{11}$ and $R^{12}$ all stand for H.
is prepared by a process comprising the steps of protecting a compound of formula (7)

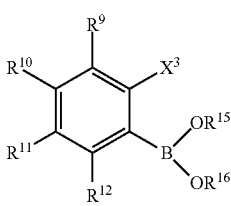
(7)

wherein $X^3$ stands for a halogen
wherein $R^9$, $R^{10}$, $R^{11}$ and $R^{12}$ all stand for H,
and wherein $R^{15}$ and $R^{16}$ each independently stand for H, alkyl or aryl,
with PG-LG, wherein PG stands for a protecting group and wherein LG stands for a leaving group to form the corresponding compound of formula (6)

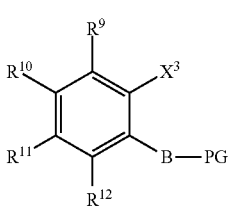
(6)

wherein $X^3$, $R^9$, $R^{10}$, $R^{11}$ and $R^{12}$ are as defined herein and wherein PG stands for the protecting group reacting the compound of formula (6) with a compound of formula (5)

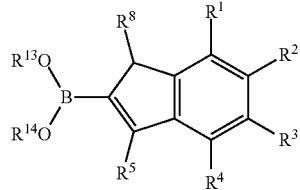
(5)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group and wherein $R^{13}$ and $R^{14}$ each independently stand for H, alkyl or aryl,
in a solvent in the presence of a Pd catalyst and a base to form the corresponding compound of formula (4)

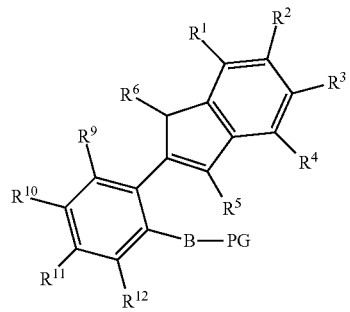
(4)

wherein $R^1$, $R^2$, $R^3$, $R^4$, $R^5$ and $R^6$, $R^9$, $R^{10}$, $R^{11}$ and $R^{12}$ and PG are as defined herein
and deprotecting the compound of formula (4) by reaction of the compound of formula (4) with an acid to form the corresponding compound of formula (1)

(1)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group
wherein $R^7$ and $R^8$ each independently stand for H, or an alkyl or aryl
and wherein $R^9$, $R^{10}$, $R^{11}$ and $R^{12}$ all stand for H.

In a special embodiment the invention relates to a process for the preparation of a compound of formula (1)

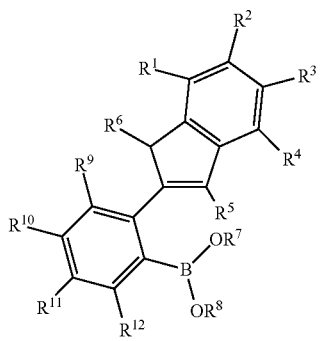

(1)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group wherein $R^7$ and $R^8$ each independently stand for H, or an alkyl or aryl
and wherein $R^9$, $R^{10}$, $R^{11}$ and $R^{12}$ all stand for H, comprising the steps of protecting a compound of formula (7)

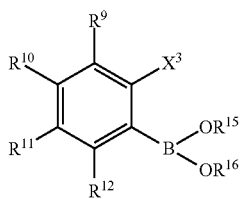

(7)

wherein $X^3$ stands for a halogen
wherein $R^9$, $R^{10}$, $R^{11}$ and $R^{12}$ all stand for H, and wherein $R^{15}$ and $R^{16}$ each independently stand for H, alkyl, or aryl, with PG-LG, wherein PG stands for a protecting group and wherein LG stands for a leaving group to form the corresponding compound of formula (6)

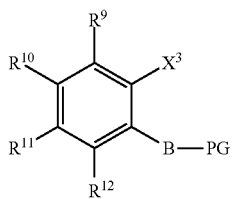

(6)

wherein $X^3$, $R^9$, $R^{10}$, $R^{11}$ and $R^{12}$ are as defined herein and wherein PG stands for the protecting group
reacting the compound of formula (6) with a compound of formula (5)

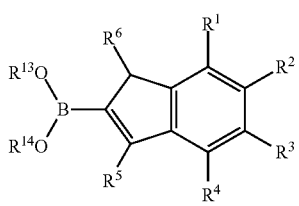

(5)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group and wherein $R^{13}$ and $R^{14}$ each independently stand for H, alkyl or aryl,
in a solvent in the presence of a Pd catalyst and a base to form the corresponding compound of formula (4)

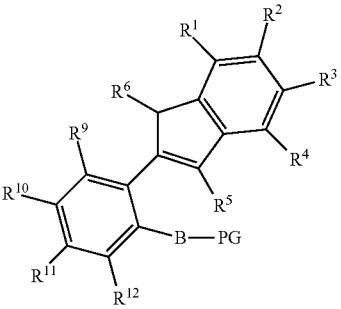

(4)

wherein $R^1$, $R^2$, $R^3$, $R^4$, $R^5$ and $R^6$, $R^9$, $R^{10}$, $R^{11}$ and $R^{12}$ and PG are as defined herein
and deprotecting the compound of formula (4) by reaction of the compound of formula (4) with an acid to form the corresponding compound of formula (1)

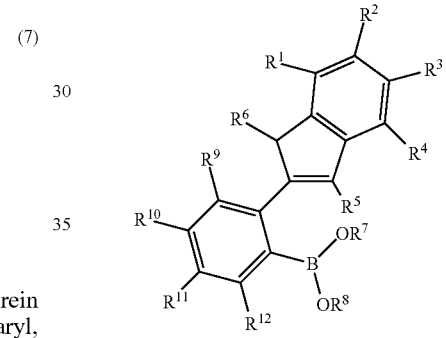

(1)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group wherein $R^7$ and $R^8$ each independently stand for H, or an alkyl or aryl
and wherein $R^9$, $R^{10}$, $R^{11}$ and $R^{12}$ all stand for H.

In yet another aspect, the invention relates to a compound of formula (1)

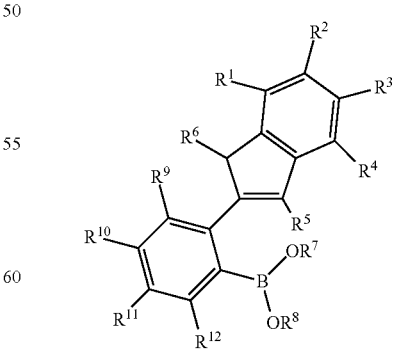

(1)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group wherein $R^7$ and $R^8$ each independently stand for H, or an alkyl or aryl
and wherein $R^9$, $R^{10}$, $R^{11}$ and $R^{12}$ all stand for H.

Preferably, in the compound of formula (1), $R^1$, $R^2$, $R^3$, $R^4$, $R^5$, $R^6$, $R^7$, $R^8$, $R^9$, $R^{10}$, $R^{11}$ and $R^{12}$ all stand for H.
$X^3$ In the compound of formula (7), $X^3$ stands for halogen, for example Fl, I, Cl or Br, preferably Br.
$R^{15}$ and $R^{16}$ In the compound of formula (7), $R^{15}$ and $R^{16}$ each independently stand for H, alkyl, for example an alkyl of 1 to 6 carbon atoms, for example methyl, ethyl, t-butyl, n-propyl or isopropyl, preferably methyl or isopropyl, or a cyclic alkyl, for example of 4 to 8 carbon atoms; aryl, preferably phenyl. Preferably $R^{15}$ and $R^{16}$ both stand for H.

In the deprotecting step, the compound of formula (7) is reacted with PG-LG, wherein PG stands for a protecting group and wherein LG stands for a leaving group, for example PG-LG stands for a 2-amino group separated by 2 to 6 carbon atoms, for example PG-LG stands for 1,8-diamino naphthalene. When a reaction with PG-LG occurs, the protecting group PG will be bound to the compound of formula (7).

The reaction conditions for the deprotecting step are in principle not critical. For example, the temperature may be chosen—depending on the choice of solvent—in the range of 100 to 150° C. The reaction is preferably performed under atmospheric pressure (1 bar).

Examples of solvents that are suitable for the deprotecting step include but are not limited to alcohols, for example methanol or ethanol; aromatic solvents, for example benzene, toluene or xylene; ethers, for example tetrahydrofuran, dioxane or dimethoxyethane; amides, for example dimethylformamide. Preferably, for the deprotecting step organic solvents, such as toluene are used.

Preferably, the molar ratio of the compound of formula (7) to PG-LG is in the range from 1:1 to 1:3, for example the molar ratio of the compound of formula (7) to PG-LG is about 1:1.6.

The compound of formula (7) is commercially available, from for example Aldrich, but can also be synthesized using methods known in the art.

The protected compound of formula (6) is then reacted with a compound of formula (5)
$R^{13}$ and $R^{14}$ In the compound of formula (5), $R^{13}$ and $R^{14}$ each independently stand for H, alkyl, for example a cyclic alkyl or an acyclic alkyl, for example a linear alkyl, for example an alkyl having 1 to 6 C-atoms, for example methyl, ethyl, t-butyl, i-propyl or n-hexane; or for aryl, for example phenyl.

Suitable solvents for the reaction of the compound of formula (6) with the compound of formula (5) include but are not limited to alcohols, for example methanol or ethanol; aromatic solvents, for example benzene, toluene or xylene; ethers, for example tetrahydrofuran, dioxane or dimethoxyethane; amides, for example dimethylformamide. Preferably organic solvents are used, more preferably aromatic solvents, more preferably toluene. Mixtures of solvents, such as the solvents mentioned herein may also be used.

The Pd catalysts that can be used in the reaction of the compound of formula (6) with the compound of formula (5) are in principle all Pd catalysts known to be suitable for Suzuki couplings. Preferably, a Pd(0) catalyst or a catalyst wherein Pd(0) is generated in situ by reduction of (more stable) Pd(II) compounds is used. Examples of Pd catalysts include tetrakis(triphenylphosphin)palladium (($Ph_3P)_4Pd$), palladium (II) acetate ($Pd(O_2CCH_3)_2$ or $Pd(Oac)_2$), tris (dibenzylideneacetone)dipalladium ($PD(dba)_2$) and bis(triphenylphosphin)palladium dichloride (($PPh_3)_2PdCl_2$), 1,1'-bis(diphenylphosphino)ferrocene]dichloropalladium(II) ($PdCl_2(dppf)$), [1,2-bis(diphenylphosphino)ethane]dichloropalladium(II), ($PdCl_2(dppe)$), bis(tricyclohexyl phosphine)palladium(0), bis(triethylphosphine)palladium(II) chloride, bis(tri-t-butylphosphine)palladium(0), bis[1,2-bis (diphenylphosphino)ethane] palladium(0), bis[tri(o-tolyl) phosphine]palladium(II) chloride, trans-benzyl(chloro)bis (triphenylphosphine)palladium(II) or Pd on carbon (Pd/C).

Preferably as Pd catalyst, tetrakis(triphenylphosphin)palladium ($Pd(PPh_3)_4$) or Pd/C is used.

The base that can be used in the reaction of the compound of formula (6) with the compound of formula (5) can in principle be any base, for example an inorganic or an organic base. Preferably an organic base is used in the preparation of the bridged bis-indenyl) ligand of formula (3), such as for example a quaternary ammonium salt, for example tetra n-butylammoniumacetate or a tertiary amine, for example triethylamine ($Et_3N$). Other examples of suitable bases include but are not limited to sodium carbonate, sodium acetate, sodium tert-butoxide, potassium carbonate, potassium iodide, sodium iodide, potassium acetate, cesium carbonate, cesium fluoride, lithium hydroxide, sodium hydroxide, sodium ethoxide, potassium fluoride and potassium phosphate.

In principle, the reaction conditions for the reaction of compound (6) with compound (5) are not critical and the temperatures, pressures and reaction time known to be suitable for Suzuki couplings, may be used by the person skilled in the art and optimal conditions can be found using routine experimentation. For example, the temperature may be from 60 to 120° C., as at temperatures below 60° C., the reaction hardly proceeds and at temperatures of above 120° C., tarring may occur. Preferably, the temperature is chosen to be at least 60, preferably at least 75 and/or at most 100, preferably at most 85° C. The pressure under which the process is performed is preferably atmospheric pressure (1 bar). The reaction time may for example be in the range from 36 to 48 hours.

The concentration of the compound of formula (6) and of the compound of formula (5) is in principle not critical, but the volume of solvent may for example be in the range from 4-10 times, for example about 6.5 times that of the sum of the weight of the compound of formula (6) and the compound of formula (5).

The step of deprotecting the compound of formula (4) to remove the protecting group PG is performed with an acid. Examples of suitable acids for said deprotection include but are not limited to acidic resins, mineral acids and organic acids, such as sulphuric acid and phosphoric acid.

The person skilled in the art is aware of which solvents can be used for the deprotection of the compound of formula (4). For example, the same solvent as for the reaction of the compound of formula (6) with the compound of formula (5) may be used, for example alcohols, for example methanol or ethanol; aromatic solvents, for example benzene, toluene or xylene; ethers, for example tetrahydrofuran, dioxane or dimethoxyethane; amides, for example dimethylformamide; or water. Preferably organic solvents are used, more preferably aromatic solvents, more preferably toluene. Mixtures of solvents, such as the solvents mentioned herein may also be used, for example a mixture of water and an aromatic solvent or a mixture of water with an alcohol such as ethanol.

The person skilled in the art knows at which temperature and pressures to perform such deprotection, for example the temperature for the deprotection may be selected in the range of 10 to 25° C. The pressure under which the process is performed is preferably atmospheric pressure (1 bar).

Preferably, the deprotection of the compound of formula (4) is performed using a molar ratio of acid to compound of formula (4) in the range from 1:1 to 4:1, for example using excess of acid, for example in a molar ratio of acid to compound of formula (4) of about 1.4:1.

Alternatively, the compound of formula (1) may be prepared using the process according to the invention further comprising the step of preparing a compound of formula (1)

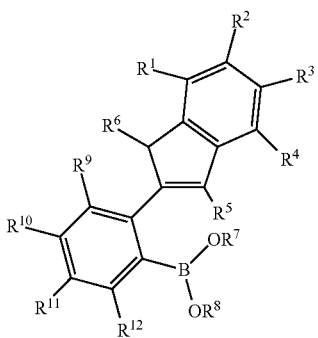

(1)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group wherein $R^7$ and $R^8$ each independently stand for H, or an alkyl or aryl
and wherein $R^9$, $R^{10}$, $R^{11}$ and $R^{12}$ all stand for H,
by a process comprising the step of reacting a compound of formula (9)

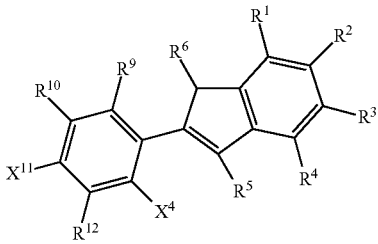

(9)

wherein $R^1$, $R^2$, $R^3$, $R^4$, $R^5$, $R^6$, $R^9$, $R^{10}$, $R^{11}$ and $R^{12}$ are as defined herein and wherein $X^4$ stands for a halogen with a compound of formula (10)

B(OR$^{17}$)$_3$        (10)

wherein $R^{17}$ stands for H or for an alkyl having 1 to 6 carbon atoms
in the presence of magnesium and an acid
to form the corresponding compound of formula (1).

The temperature for this process is preferably chosen in the range from 15 to 35 C. The pressure chosen is preferably atmospheric pressure (1 bar). The solvent chosen is preferably an organic solvent, for example tetrahydrofuran (THF).

Preferably, the compound of formula (9) and the compound of formula (10) are used in a solvent, wherein the volume of solvent: the total weight of the compound of formula (9) and the compound of formula (10) is chosen in the ratio from 8:1-12:1. Preferably, the compound of formula (10) and the compound of formula (9) are used in a molar ratio of the compound of formula (10) to the compound of formula (9) in the range from 4:1 to 1:1, preferably about 2:1.

In another aspect, the invention relates to a process for the preparation of a compound of formula (1)

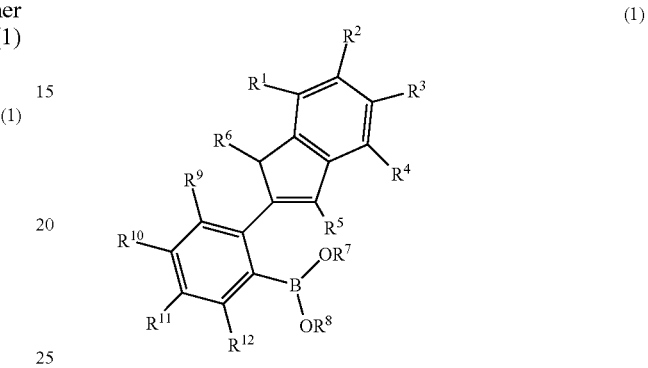

(1)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group wherein $R^7$ and $R^8$ each independently stand for H, or an alkyl or aryl
and wherein $R^9$, $R^{10}$, $R^{11}$ and $R^{12}$ all stand for H,
comprising the step of reacting a compound of formula (9)

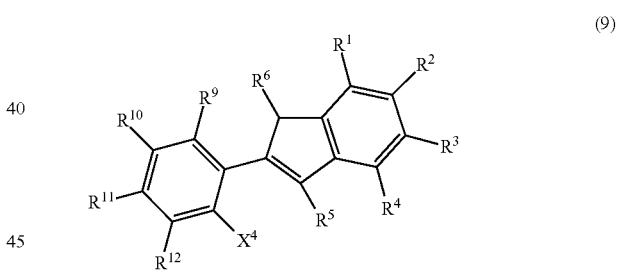

(9)

wherein $R^1$, $R^2$, $R^3$, $R^4$, $R^5$, $R^6$, $R^9$, $R^{10}$, $R^{11}$ and $R^{12}$ are as defined herein and wherein $X^4$ stands for a halogen with a compound of formula (10)

B(OR$^{17}$)$_3$        (10)

wherein $R^{17}$ stands for H or for an alkyl having 1 to 6 carbon atoms
in the presence of magnesium and an acid
to form the corresponding compound of formula (1)
$X^4$ In the compound of formula (9), $X^4$ stands for a halogen, for example Fl, Cl or Br, preferably for Br.

In this process, the compound of formula (9) is reacted with a compound of formula (10)

B(OR$^{17}$)$_3$        (10)

wherein $R^{17}$ stands for H or for an alkyl having 1 to 6 carbon atoms, for example methyl, n-butyl, propyl or isopropyl, in the presence of magnesium and an acid.

Examples of acids suitable for the reaction of the compound of formula (9) with the compound of formula (10) to form the corresponding compound of formula (1) include but are not limited to inorganic acids, for example HCl, mineral acids and acidic resins.

In another embodiment, the invention also relates to a process for the preparation of the compound of formula (1), $R^7$ and $R^8$ form a ring together with the oxygen atoms to which they are bound. Specifically, the invention relates to a process according to the invention, further comprising the step of preparing the compound of formula (1)

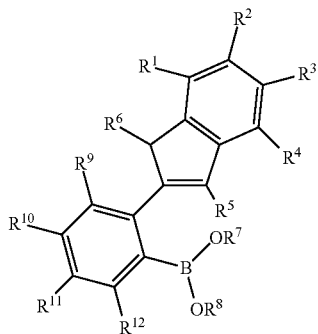

(1)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group wherein $R^7$ and $R^8$ form a ring together with the oxygen atoms to which they are bound
and wherein $R^9$, $R^{10}$, $R^{11}$ and $R^{12}$ all stand for H,
by a process comprising the steps of reacting a compound of formula (12)

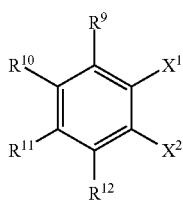

(12)

wherein $R^9$, $R^{10}$, $R^{11}$ and $R^{12}$ all stand for H,
and wherein $X^1$ and $X^2$ are each independently chosen from the group of halogens and preferably wherein $X^1$ and $X^2$ are not the same
with a compound of formula (5)

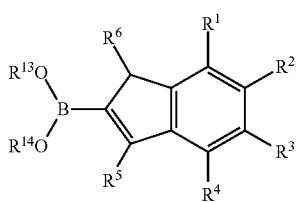

(5)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group and wherein $R^{13}$ and $R^{14}$ each independently stand for H, alkyl or aryl in a solvent in the presence of a Pd catalyst and a base to form the corresponding compound of formula (13)

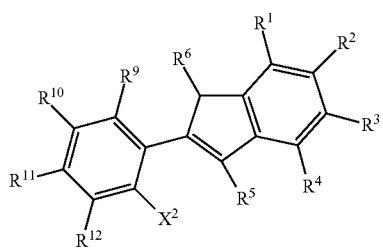

(13)

wherein $R^1$, $R^2$, $R^3$, $R^4$, $R^5$, $R^6$, $R^9$, $R^{10}$, $R^{11}$, $R^{12}$ and $X^2$ are as defined herein
reacting the compound of formula (13) with a compound of formula (14)

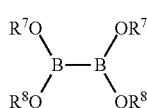

(14)

in a solvent, in the presence of a Nickel (II) or Nickel (0) catalyst, a ligand for the Nickel (II) or Nickel (0) catalyst and a base to form the corresponding compound of formula (1),

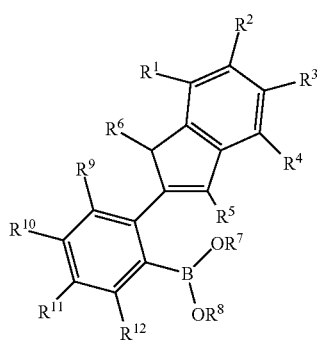

(1)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group wherein $R^7$ and $R^8$ form a ring together with the oxygen atoms to which they are bound and wherein $R^9$, $R^{10}$, $R^{11}$ and $R^{12}$ all stand for H.

In another aspect, the invention relates to a process for the preparation of a compound of formula (1)

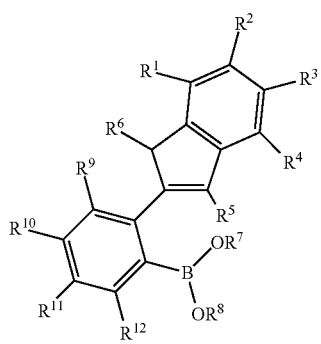

(1)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group wherein $R^7$ and $R^8$ form a ring together with the oxygen atoms to which they are bound comprising the steps of reacting a compound of formula (12X)

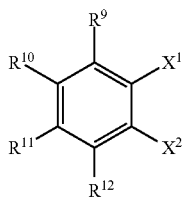
(12X)

wherein $R^9$, $R^{10}$, $R^{11}$ and $R^{12}$ all stand for H,
and wherein $X^1$ and $X^2$ are each independently chosen from the group of halogens and preferably wherein $X^1$ and $X^2$ are not the same
with a compound of formula (5)

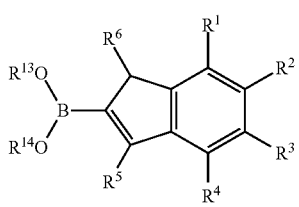
(5)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group and wherein $R^{13}$ and $R^{14}$ each independently stand for H, alkyl or aryl,
in a solvent in the presence of a Pd catalyst and a base to form the corresponding compound of formula (13)

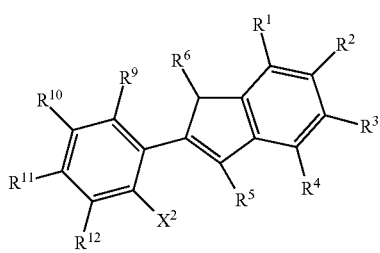
(13)

wherein $R^1$, $R^2$, $R^3$, $R^4$, $R^5$, $R^6$, $R^9$, $R^{10}$, $R^{11}$, $R^{12}$ and $X^2$ are as defined herein
reacting the compound of formula (13) with a compound of formula (14X)

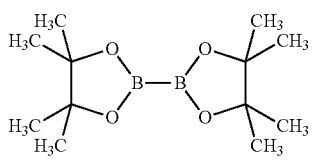
(14X)

in a solvent, in the presence of a Nickel (II) or Nickel (0) catalyst, a ligand for the Nickel (II) or Nickel (0) catalyst and a base to form the corresponding compound of formula (1X).

In yet another aspect, the invention relates to the novel compound of formula (1X)

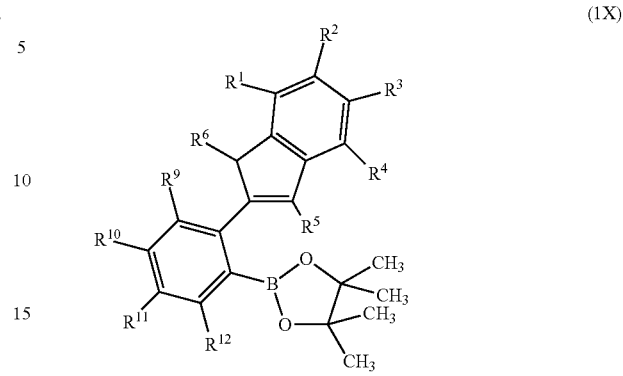
(1X)

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group and wherein $R^9$, $R^{10}$, $R^{11}$ and $R^{12}$ all stand for H.

Preferably, the invention relates to the compound of formula (1X), wherein $R^1$, $R^2$, $R^3$, $R^4$, $R^5$, $R^6$, $R^9$, $R^{10}$, $R^{11}$ and $R^{12}$ all stand for H.

$X^1$ and $X^2$

In the compound of formula (12), $X^1$ and $X^2$ are each independently chosen from the group of halogens, for example F, Cl, Br, preferably Cl and Br. Preferably $X^1$ and $X^2$ are not the same. Preferably, $X^1$ stands for Br and $X^2$ stands for Cl.

The Pd catalysts that can be used in the reaction of compound of formula (12) with the compound of formula (5) are in principle all Pd catalysts known to be suitable for Suzuki couplings. Preferably, a Pd(0) catalyst or a catalyst wherein Pd(0) is generated in situ by reduction of (more stable) Pd(II) compounds is used. Examples of Pd catalysts include tetrakis(triphenylphosphin)palladium (($Ph_3P$)$_4$Pd), palladium (II) acetate ($Pd(O_2CCH_3)_2$ or $Pd(Oac)_2$), tris (dibenzylideneacetone)dipalladium ($PD(dba)_2$) and bis(triphenylphosphin)palladium dichloride (($PPh_3$)$_2PdCl_2$), 1,1'-bis(diphenylphosphino)ferrocene]dichloropalladium(II) ($PdCl_2$(dppf)), [1,2-bis(diphenylphosphino)ethane]dichloropalladium(II), ($PdCl_2$(dppe)), bis(tricyclohexyl phosphine)palladium(0), bis(triethylphosphine)palladium(II) chloride, bis(tri-t-butylphosphine)palladium(0), bis[1,2-bis (diphenylphosphino)ethane] palladium(0), bis[tri(o-tolyl) phosphine]palladium(II) chloride, trans-benzyl(chloro)bis (triphenylphosphine)palladium(II).

Preferably the Pd catalyst is chosen from the group of $PdCl_2$(dppf), $PdCl_2$(dppe), bis(tricyclohexyl phosphine)palladiume(0), bis(triethylphosphine)palladium(II) chloride, bis(tri-t-butylphosphine)palladium(0), bis[1,2-bis(diphenylphosphino)ethane] palladium(0), bis[tri(o-tolyl)phosphine] palladium(II) chloride and trans-Benzyl(chloro)bis(triphenylphosphine)palladium(II).

The base that can be used in the reaction of the compound of formula (12) with the compound of formula (5) can in principle be any base, for example an inorganic or an organic base. Preferably an organic base is used in the preparation of the bridged bis-indenyl) ligand of formula (3), such as for example a quaternary ammonium salt, for example tetra n-butylammoniumacetate or a tertiary amine, for example triethylamine ($Et_3N$) or tetrabutyl ammonium hydroxide. Preferably tetrabutyl ammonium hydroxide is used as the base in the reaction of the compound of formula (12) with the compound of formula (5). Other examples of suitable bases include but are not limited to sodium tert-butoxide, potassium carbonate, lithium hydroxide, sodium hydroxide, sodium ethoxide, potassium fluoride and potassium phosphate.

Other examples of suitable bases include but are not limited to sodium carbonate, sodium acetate, sodium tert-butoxide, potassium carbonate, potassium iodide, sodium iodide, potassium acetate, cesium carbonate, cesium fluoride, lithium hydroxide, sodium hydroxide, sodium ethoxide, potassium fluoride and potassium phosphate.

Suitable solvents for the reaction of the compound of formula (12) with the compound of formula (5) include but are not limited to alcohols, for example methanol or ethanol; aromatic solvents, for example benzene, toluene or xylene; ethers, for example tetrahydrofuran, dioxane or dimethoxyethane; amides, for example dimethylformamide or water that is preferably substantially free of oxygen. Preferably organic solvents are used, more preferably aromatic solvents, more preferably toluene. Mixtures of solvents, such as the solvents mentioned herein may also be used.

In principle, the reaction conditions for the reaction of the compound of formula (12) or of the compound of formula (12X) with the compound of formula (5) are not critical and the temperatures, pressures and reaction time known to be suitable for Suzuki couplings, may be used by the person skilled in the art and optimal conditions can be found using routine experimentation. For example, the temperature may be from 60 to 120° C., as at temperatures below 60° C., the reaction hardly proceeds and at temperatures of above 120° C., tarring may occur. Preferably, the temperature is chosen to be at least 60, preferably at least 75 and/or at most 100, preferably at most 85° C. The pressure under which the process is performed is preferably atmospheric pressure (1 bar). The reaction time may for example be in the range from 36 to 48 hours.

The molar ratio of the compound of formula (12) or of the compound of formula (12X) to the compound of formula (5) is preferably chosen in the range from 1:1 to 1:3, for example in a molar ratio of about 1:1.2.

The concentration of the compound of formula (12) or of the compound of formula (12X) and of the compound of formula (5) is in principle not critical, but the volume of solvent may for example be in the range from 3-5 times, for example about 4.4 times that of the sum of the weight of the compound of formula (12) or the compound of formula (12X) and the compound of formula (5).

The compound of formula (13) that is produced in the reaction of the compound of formula (12) or of the compound of formula (12X) with the compound of formula (5) is then reacted with the compound of formula (14) in the presence of a Nickel (II) or Nickel (0) catalyst, a ligand for the Nickel (II) or Nickel (0) catalyst and a base, for example triethylamine.

Examples of ligands for the nickel catalyst include but are not limited to triphenylphosphine ($PPh_3$), 1,3-Bis(diphenylphosphino)propane (dppp), 1,2-Bis(diphenylphosphino)ethane (dope), 1,2-Bis(dimethylphosphino)ethane (dmpe), 1,4-Bis(diphenylphosphino)butane (dppb).

Examples of Nickel (II) or Nickel (0) catalyst and ligand combinations that are suitable for the reaction of the compound of formula (13) with the compound of formula (14) include but are not limited to bis(1,5-cyclooctadiene) nickel (0) (Ni(COD)$_2$), nickel(II) acetylacetonate (Ni(acac)2), Dichloro[1,3-bis(diphenylphosphino)propane]nickel (NiCl2-dppp), bis(Acetonitrile) dichloro nickel(II)(Ni(MeCN)2Cl2), allylchloro-[1,3-bis-(diisopropylphenyl)-imidazole-2-ylidene] nickel(II) ((iPr)Ni(allyl)Cl), bis(tricyclohexyl phosphine) dichloro nickel(II) (NiCl2(PCy3)2), nickel(II) chloride hexahydrate (NiCl2 hexahydrate), nickel (II) bromide hexahydrate (NiBr2 hexahydrate), bis(triphenylphosphine)nickel(II)chloride, tetrakis(triphenylphosphine)nickel(0) and 1,2-bis(dicyclohexylphosphino)ethane nickel(II) chloride.

Examples of bases that are suitable for the reaction of the compound of formula (13) with the compound of formula (14) include but are not limited to organic and inorganic bases, for example trimethyl amine, potassium carbonate, sodium carbonate, sodium acetate, potassium iodide, sodium iodide, potassium acetate, lithium hydroxide, cesium carbonate, cesium fluoride, sodium hydroxide, sodium ethoxide, potassium fluoride, potassium phosphate, tetra n-butylammoniumacetate, tetrabutyl ammonium hydroxide, tetrabutyl ammonium hydroxide, sodium tert-butoxide, potassium carbonate or lithium hydroxide.

Preferably, the solvent that is used for the reaction of the compound of formula (13) with the compound of formula (14) or the compound of formula (14X) is an organic solvent, such as for example an alcohol, for example methanol or ethanol, an aromatic solvent, for example toluene; an ether or an amide. Preferably the solvent that is used for the reaction of the compound of formula (13) with the compound of formula (14) or the compound of formula (14X) is methanol or ethanol.

The temperature for the reaction of the compound of formula (13) with the compound of formula (14) or the compound of formula (14X) is preferably chosen in the range from 40 to 100° C. The reaction is preferably performed under atmospheric pressure (1 bar)

Preferably the molar ratio of the compound of formula (13) to the compound of formula (14) or the compound of formula (14X) is chosen in the range from 1:1 to 1:3, for example about 1:1.15. The concentration of the compound of formula (13) and of the compound of formula (14) or the compound of formula (14X) is in principle not critical, but the volume of solvent may for example be in the range from 3-5 times, for example about 4.4 times that of the sum of the weight of the compound of formula (13) and the compound of formula (14) or the compound of formula (14X).

The compound of formula (2) can be prepared using methods known in the art, for example as described in U.S. Pat. No. 6,342,622, hereby incorporated by reference.

For the syntheses as described herein, the separation of products from unreacted reactants and the purification of intermediates in the synthetic process is generally not required. Preferably, however, the compound of formula (13) is purified, for example using a high vacuum distillation before it is reacted with the compound of formula (14) or the compound of formula (14X) to form the corresponding compound of formula (1) respectively the compound of formula (1X).

The process of the invention may further comprise the step of converting the compound of formula (3)

(3)

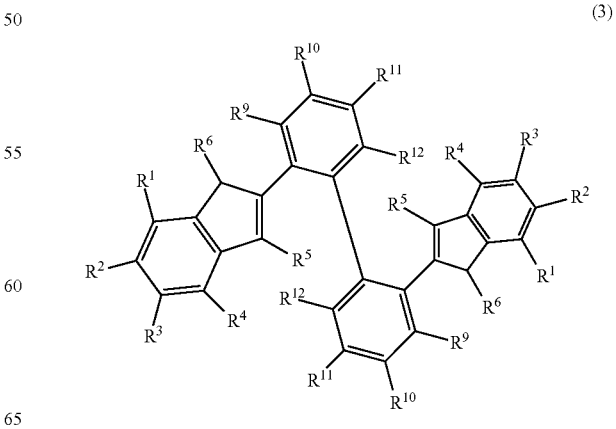

wherein $R^1$, $R^2$, $R^3$, $R^4$, $R^5$ and $R^6$ each independently stand for H, a hydrocarbon radical having 1-20 C-atoms, a halide, an alkoxy group having 1-6 C-atoms, an alkylsulphide, an amine, a Si or B-containing group or a P-containing group wherein $R^7$ and $R^8$ each independently stand for H, or an alkyl or aryl or wherein $R^7$ and $R^8$ may form a ring together with the oxygen atoms to which they are bound
and wherein $R^9$, $R^{10}$, $R^{11}$ and $R^{12}$ all stand for H, into the corresponding metallocene complex of formula (15)

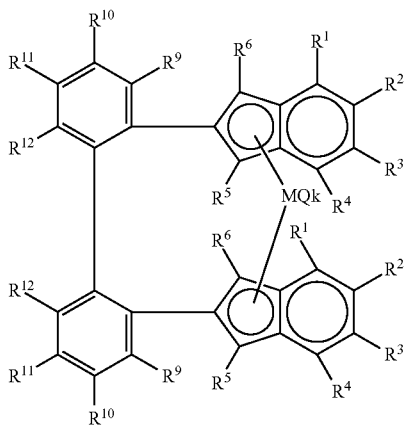

(15)

wherein $R^1$, $R^2$, $R^3$, $R^4$, $R^5$, $R^6$, $R^9$, $R^{10}$, $R^{11}$ and $R^{12}$ are as defined herein
wherein M stands for a transition metal from the group of lanthanides or from group 3, 4, 5 or 6 of the Periodic System of Elements,
wherein Q stands for an anionic ligand to M,
and wherein k is an integer and stands for the number of anionic ligands.

In the metallocene complex of formula (15)

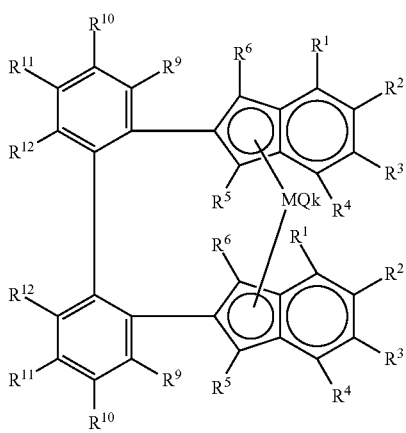

(15)

$R^1$, $R^2$, $R^3$, $R^4$, $R^5$, $R^6$, $R^9$, $R^{10}$, $R^{11}$ and $R^{12}$ are as defined herein, M stands for a transition metal from the group of lanthanides or from group 3, 4, 5 or 6 of the Periodic System of Elements, Q stands for an anionic ligand to M, and k is an integer and stands for the number of anionic ligands.

For example, a metallocene complex of formula (15) may be prepared in a two-step procedure as for example described in EP1059300A1, hereby incorporated by reference. Specifically in paragraph [0036] of EP1059300A1, it is described that the compound of formula (3) may first be converted into its dianion using for example an organometallic compound, an amine, a metal hydride, an alkaline earth metal or an alkaline earth metal. Organolithium, organomagnesium and organosodium compound may for example be used, but also sodium or potassium. Organolithium compounds, such as methyl-lithium or n-butyllithium are particularly suitable for converting the compound of formula (3) into its dianion.

In paragraph [0037] of EP1059300A1, it is described that the dianion corresponding to a bridged bis(indenyl) ligand may be converted into the corresponding metallocene complex by transmetalation with a compound of transition metal M, wherein M is as defined herein. See for example EP-A-420436 or EP-A-427697. The process described in NL-A-91011502 is particularly suitable. Examples of compounds of transition metal M include but are not limited to $TiCl_4$, $ZrCl_4$, $HfCl_4$, $Zr(OBu)_4$ and $Zr(OBu)_2Cl_2$. The transmetalation may be carried out as in NL-A-91011502 in a solvent or in a combination of solvents that weakly coordinate to transition metals from the groups 3, 4, 5, or 6 of the Periodic System of Elements with at most 1 mole equivalent, relative to the transition metal compound started from, of a Lewis base of which the conjugated acid has a $pK_a$ greater than −2.5. Examples of solvents/dispersants ($pK_a$ of conjugated acid=<−2.5) that may suitably be used in such transmetalation include but are not limited to ethoxyethane, dimethoxyethane, isopropoxyisopropane, n-propoxy-n-propane, methoxybenzene, methoxymethane, n-butoxy-n-butane, ethoxy-n-butane and dioxane. Part of the reaction medium used for the transmetalation may consist of hydrocarbons (hexane and the like).

In particular, the invention further relates to a process for the preparation of a compound of formula (15), wherein the compound of formula (3) is converted into its corresponding dianion using an organometallic compound, an amine, a metal hydride, an alkaline earth metal or an alkaline earth metal and wherein the formed dianion is transmetalated with a compound of transition metal M, to form the corresponding metallocene complex of formula (15).

Transition Metal M

The transition metal M is selected from the lanthanides or from group 3, 4, 5 or 6 of the Periodic System of Elements. The Periodic System of Elements is understood to be the new IUPAC version as printed on the inside cover of the Handbook of Chemistry and Physics, 70th edition, CRC Press, 1989-1990.

Preferably, M stands for Ti, Zr, Hf, V or Sm, more preferably for Ti, Zr, Hf, more preferably for preferably for Zr or Hf, even more preferably for Zr. Complexes of formula (15), wherein M stands for Zr or Hf metallocene may suitably be used as catalysts in the synthesis of polyethylene or the synthesis of polypropylene. Please note that the expression 'synthesis/preparation of polyethylene' referred herein is defined as homopolymerization or copolymerization of ethylene with one or more α-olefins having 3-12 C-atoms and optionally one or more non-conjugated dienes.

Anionic Ligand Q

Q stands for an anionic ligand to the transition metal M. The anionic ligand may comprise one or more uni- or polyvalent anionic ligands. Examples of such ligands include but are not limited to a hydrogen atom, a halogen atom, an alkyl group, an aryl group, an aralkyl group, an alkoxy group, an aryloxy group and a group with a heteroatom chosen from group 14, 15 or 16 of the Periodic System of Elements, such as for example an amine group or amide group; a sulphur containing group, for example sulphide or sulphite; a phosphorus containing group, for example phosphine or phosphite.

Q may also be a monoanionic ligand bonded to the transition metal M via a covalent metal-carbon bond and which is additionally capable to non-covalently interact with M via one of more functional groups. The functional group mentioned above can be one atom, but also a group of atoms connected together. The functional group is preferably an atom of group 17 of the Periodic Table of Elements or a group containing one or more elements from groups 15, 16 or 17 of the Periodic Table of Elements. Examples of functional groups are F, Cl, Br, dialkylamino and alkoxy groups.

Q may for example be a phenyl group in which at least one of the ortho-positions is substituted with a functional group capable of donating electron density to the transition metal M. Q may also be a methyl group in which one or more of the alpha-positions is substituted with a functional group capable of donating electron density to the transition metal M. Examples of methyl groups substituted in one or more of the alpha-positions are benzyl, diphenylmethyl, ethyl, propyl and butyl substituted with a functional group capable of donating electron density to the transition metal M. Preferably at least one of the ortho-positions of a benzyl-group is substituted with a functional group capable of donating electron density to the transition metal M.

Examples of these Q groups include, but are not limited to: 2,6-difluorophenyl, 2,4,6-trifluorophenyl, pentafluorophenyl, 2-alkoxyphenyl, 2,6-dialkoxyphenyl, 2,4,6-tri(trifluoromethyl)phenyl, 2,6-di(trifluoromethyl)phenyl, 2-trifluoromethylphenyl, 2-(dialkylamino)benzyl and 2,6-(dialkylamino)phenyl.

Q may for example stand for a mono-anionic ligand, for example for methyl of Cl, preferably for Cl.

Integer k

The number of Q groups in the metallocene complex of formula (15) (represented by the integer k in formula (6)) is determined by the valence of the transition metal M and the valence of the Q groups. In the metallocene complex of formula (6), k is equal to the valence of M minus 2 divided by the valence of Q. For example, in case M stands for Zr and Q stands for Cl, k is 2.

In a preferred embodiment, the metallocene complex of formula (15) is [2,2'-bis(2-indenyl)biphenyl]ZrCl$_2$.

The metallocene complex of formula (15) may be used, optionally in the presence of a cocatalyst for the polymerization of one or more α-olefins, preferably for the polymerization of ethylene, for example in solution or suspension polymerization of ethylene.

The α-olefin(s) is/are preferably chosen from the group comprising ethylene, propylene, butene, pentene, hexene, heptene and octene, while mixtures can also be used. More preferably, ethylene and/or propylene is/are used as α-olefin. The use of such α-olefins leads to the formation of crystalline polyethylene homopolymers and copolymers of both low and high density (HDPE, LDPE, LLDPE, etc.), and polypropylene homopolymers and copolymers (PP and EMPP). The monomers needed for such products and the processes to be used are known to the skilled in the art.

The metallocene complex of formula (15) is also suitable for the preparation of amorphous or rubbery copolymers based on ethylene and another α-olefin. Propylene is preferably used as the other α-olefin, so that EPM rubber is formed.

Details of such use and examples of cocatalysts may be found in EP 1059300 A1, paragraphs [0038]-[0057]; hereby incorporated by reference.

Cocatalyst

The cocatalyst for the polymerization of one or more α-olefins can be an organometallic compound. The metal of the organometallic compound can be selected from group 1, 2, 12 or 13 of the Periodic Table of Elements. Suitable metals include sodium, lithium, zinc, magnesium, and aluminium, preferably aluminium. At least one hydrocarbon radical is bonded directly to the metal to provide a carbon-metal bond. The hydrocarbon group used in such compounds preferably contains 1-30, more preferably 1-10 carbon atoms. Examples of suitable compounds include, amyl sodium, butyl lithium, diethyl zinc, butyl magnesium chloride, and dibutyl magnesium. Preference is given to organoaluminium compounds, including, for example and without limitation, the following: trialkyl aluminium compounds, such as triethyl aluminium and tri-isobutyl aluminium; alkyl aluminium hydrides, such as diisobutyl aluminium hydride; alkylalkoxy organoaluminium compounds; and halogen-containing organoaluminium compounds, such as diethyl aluminium chloride, diisobutyl aluminium chloride, and ethyl aluminium sesquichloride. Preferably, aluminoxanes are selected as the organoaluminium compound. Most preferably, methylaluminoxane (MAO) is used as the cocatalyst.

The aluminoxanes can also be aluminoxanes containing a low amount of trialkylaluminium; preferably 0.5 to 15 mol % trialkylaluminium. In this case the amount of trialkylaluminium is more preferably 1-12 mol % trialkylaluminium.

In addition or as an alternative to the organometallic compounds as the cocatalyst, the polymerization may be performed in the presence of a compound which contains or yields in a reaction with the metallocene complex of formula (15), a non-coordinating or poorly coordinating anion. Such compounds have been described for instance in EP-A-426,637, the complete disclosure of which is incorporated herein by reference. Such an anion is bonded sufficiently unstably such that it is replaced by an unsaturated monomer during the copolymerization. Such compounds are also mentioned in EP-A-277,003 and EP-A-277,004, the complete disclosures of which are incorporated herein by reference. Such a compound preferably contains a friaryl borane or a tetraaryl borate or an aluminium or silicon equivalent thereof. Examples of suitable cocatalyst compounds include, without limitation, the following:

dimethyl anilinium tetrakis (pentafluorophenyl) borate $[C_6H_5N(CH_3)_2H]+[B(C_6F_5)_4]^-$;
dimethyl anilinium bis (7,8-dicarbaundecaborate)-cobaltate (III);
tri(n-butyl)ammonium tetraphenyl borate;
triphenylcarbenium tetrakis (pentafluorophenyl) borate;
dimethylanilinium tetraphenyl borate;
tris(pentafluorophenyl) borane; and
tetrakis(pentafluorophenyl) borate.

As described for instance in EP-A-500,944, the complete disclosure of which is incorporated herein by reference, the reaction product of a halogenated transition metal complex and an organometallic compound, such as for instance triethyl aluminium (TEA), can also be used.

The molar ratio of the cocatalyst relative to the transition metal complex (metallocene complex of formula (6)), in case an organometallic compound is selected as the cocatalyst, usually is in a range of from about 1:1 to about 10,000:1, and preferably is in a range of from about 1:1 to about 2,500:1. If a compound containing or yielding a non-coordinating or poorly coordinating anion is selected as cocatalyst, the molar ratio usually is in a range of from about 1:100 to about 1,000:1, and preferably is in a range of from about 1:2 to about 250:1.

The metallocene complex of formula (15) as well as the cocatalyst may be used in the polymerizations of α-olefins as a single component or as a mixture of several components. As is known to the person skilled in the art, a mixture may for instance be desired where there is a need to influence the molecular properties of the polymer, such as molecular weight and in particular molecular weight distribution.

The metallocene complex of formula (15) can be used supported as well as non-supported. The supported catalysts are used mainly in gas phase and slurry processes. The carrier used may be any carrier known as carrier material for catalysts, for instance silica, alumina or $MgCl_2$. Preferably, the carrier material is silica.

Support

The catalyst complex of formula (15) can be used supported as well as non-supported. The carrier used may be any carrier known as carrier material for catalysts. For instance, the support in the catalyst composition of the present invention can be an organic or inorganic material and is preferably porous. Examples of organic material are cross-linked or functionalized polystyrene, PVC, cross-linked polyethylene. Examples of inorganic material are silica, alumina, silica-alumina, inorganic chlorides such as $MgCl_2$, talc and zeolite. Mixtures of two or more of these supports may also be used. The preferred particle size of the support is from 1 to 120 micrometers, preferably of from 20 to 80 micrometers and the preferred average particle size is from 40 to 50 micrometers.

The preferred support is silica. The pore volume of the support is preferably of from 0.5 to 3 $cm^3/g$. The preferred surface area of the support material is in the range of from 50 to 500 $m^2/g$. The silica used in this invention is preferably dehydrated prior to being used to prepare the catalyst composition.

Therefore, the process of the present invention may further comprise the step(s) of
  combining in a solvent a support material, the catalyst complex of formula (15) (also referred to herein as the compound of formula (15)) to form the supported catalyst and
  optionally drying the supported catalyst.

Further details on the synthesis of the (supported) catalyst can be found in EP1059300A1, hereby incorporated by reference or in WO2013/097936A1, hereby also incorporated by reference.

Polymerization of α-olefins can be effected in a known manner, in the gas phase as well as in a liquid reaction medium. In the latter case, both solution and suspension polymerization are suitable, while the quantity of transition metal to be used generally is such that its concentration in the dispersion agent amounts to $10^{-8}$-$10^{-4}$ mol/l, preferably $10^{-7}$-$10^{-3}$ mol/l.

The production processes of LLDPE are summarised in "Handbook of Polyethylene" by Andrew Peacock (2000; Dekker; ISBN 0824795466) at pages 43-66.

The polymerizations using the metallocene complex of formula (15) will hereafter be explained in further detail with reference to a polyethylene preparation known per se, which is representative of the α-olefin polymerizations meant here. For the preparation of other polymers on the basis of an α-olefin, the reader is expressly referred to the multitude of publications on this subject.

The preparation (polymerization) of polyethylene referred to herein is defined as homopolymerization or copolymerization of ethylene with one or more α-olefins having 3-12 carbon atoms and optionally one or more non-conjugated dienes. The α-olefins that are particularly suitable include propylene, butane, for example 1-butene; hexane, for example 1-hexene; and octene. Suitable dienes include for instance 1,7-octadiene and 1,9-decadiene.

Any liquid that is inert relative to the catalyst system (the metallocene complex of formula (15) and the optional cocatalyst) may be used as dispersion agent in the polymerization. One or more saturated, straight or branched aliphatic hydrocarbons, such as butanes, pentanes, hexanes, heptanes, pentamethyl heptane or mineral oil fractions such as light or regular petrol, naphtha, kerosine or gas oil are suitable for that purpose. Aromatic hydrocarbons, for instance benzene and toluene, can be used, but because of their cost as well as on account of safety considerations, it will be preferred not to use such solvents for production on a technical scale. In polymerization processes on a technical scale, it is preferred therefore to use as solvent the low-priced aliphatic hydrocarbons or mixtures thereof, as marketed by the petrochemical industry. If an aliphatic hydrocarbon is used as solvent, the solvent may yet contain minor quantities of aromatic hydrocarbon, for instance toluene. Thus, if for instance methyl aluminoxane (MAO) is used as cocatalyst, toluene can be used as solvent in order to supply the MAO in dissolved form to the polymerization reactor. Drying or purification is desirable if such solvents are used; this can be done without problems by the average person skilled in the art.

A solution polymerization is preferably carried out at temperatures between 150° C. and 250° C.; in general, a suspension polymerization takes place at lower temperatures, preferably below 100° C.

The polymer solution resulting from the polymerization can be worked up by a method known per se. In general the catalyst system is de-activated at some point during the processing of the polymer. The deactivation is also effected in a manner known per se, e.g. by means of water or an alcohol. Removal of the catalyst system residues can usually be omitted when the quantity of metallocene complex of formula (15) in the polymer, in particular the content of halogen and transition metal is very low.

Polymerization can be effected at atmospheric pressure, but also at an elevated pressure of up to 500 MPa, continuously or discontinuously. If the polymerization is carried out under pressure, the yield of polymer can be increased additionally, resulting in an even lower catalyst residue content. Preferably, the polymerization is performed at pressures between 0.1 and 25 MPa. Higher pressures, of 100 MPa and upwards, can be applied if the polymerization is carried out in so-called high-pressure reactors. In such a high-pressure process the metallocene complex of formula (15) can also be used with good results.

The polymerization can also be performed in several steps, in series as well as in parallel. If required, the catalyst composition, temperature, hydrogen concentration, pressure, residence time, etc. may be varied from step to step. In this way it is also possible to obtain products with a wide molecular weight distribution.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention is now elucidated by way of the following examples, without however being limited thereto.

Comparative Experiments

Process for Synthesis of [2,2'-Bis(2-indenyl)biphenyl] from Ortho-Bromo-(2-indenyl)Benzene (OBPI) or Ortho-Iodo-(2-indenyl)Benzene (OIPI)

Reaction-1:

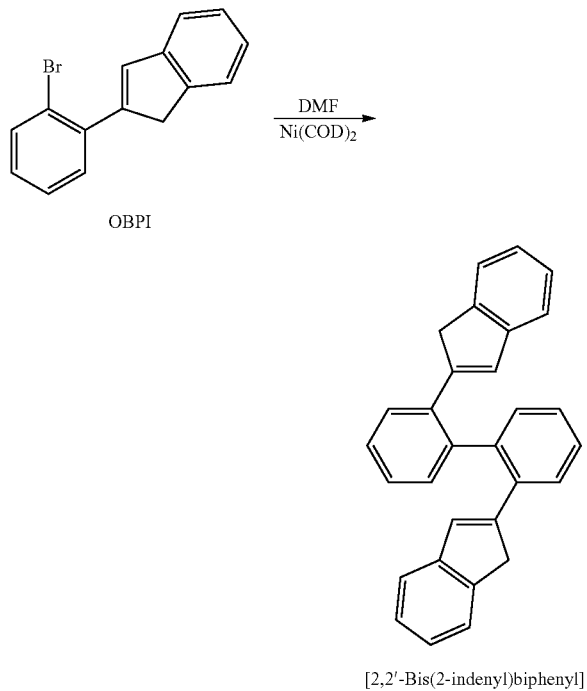

[2,2'-Bis(2-indenyl)biphenyl]

Procedure:

In 10 ml round bottom flask (RBF), OBPI (0.10 g), Ni(COD)$_2$ (0.05 g) and DMF (5 ml) were added. The mixture was slowly stirred and heated up to 100° C. for 2 hrs. Then a sample of the solution was submitted for HPLC analysis. The HPLC result showed the formation of phenyl indene (impurity) and presence of unreacted OBPI. Not even traces of [2,2'-Bis(2-indenyl)biphenyl] (the desired product) formation could be detected. The same reaction was carried out with OIPI instead of OBPI but the desired product was again not obtained.

Reaction-2:

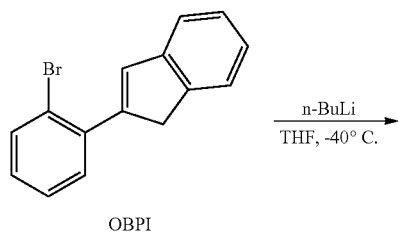

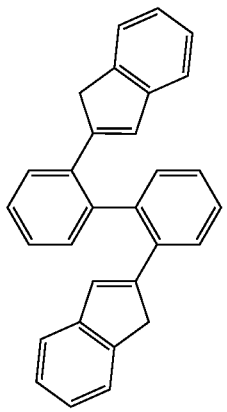

[2,2'-Bis(2-indenyl)biphenyl]

Procedure:

In a 25 ml RBF, OBPI (0.5 g), 10 ml THF were added and cooled to −40° C. Then n-BuLi (2.0 ml) was added slowly. During this addition, temperature raised up to −35° C. After addition, the solution maintained at −40° C. for 30 min and then slowly the temperature was raised up to 0° C. and water (5 ml) was added slowly. Then Dichloromethane (10 ml) was added. Two phases were separated and the organic phase was dried over sodium sulphate. The solvent was then finally removed by distillation using rotary evaporator. The residue submitted for HPLC analysis. The HPLC result did show that instead of desired product only phenyl indene (impurity) was formed.

Reaction-3:

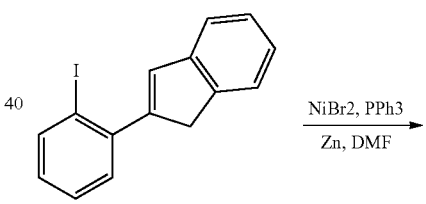

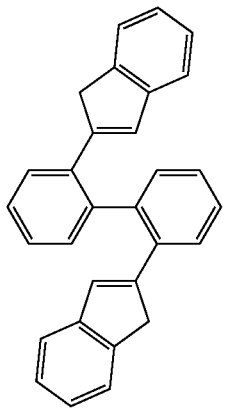

[2,2'-Bis(2-indenyl)biphenyl]

Procedure:

To a 50 ml RBF, OIPI (0.1 g), NiBr$_2$ (0.68 g), PPh$_3$ (0.329 g), Zn (0.02 g) and DMF (10 ml) were added. The reaction mass purged with nitrogen and heated up to 110° C. for overnight. The progress of reaction was monitored by TLC. The formation of desired product was found. However, a sample submitted for HPLC analysis showed that only a very low amount of desired product was formed (3.33%).

The reaction above was also tried with different temperatures (50° C. and 80° C.) and different catalyst compositions (NiCl$_2$ and Pd(PPh$_3$)$_4$) also. But results showed that only 3-4% product formation and/or formation of impurities (phenyl indene)

Reaction-4:

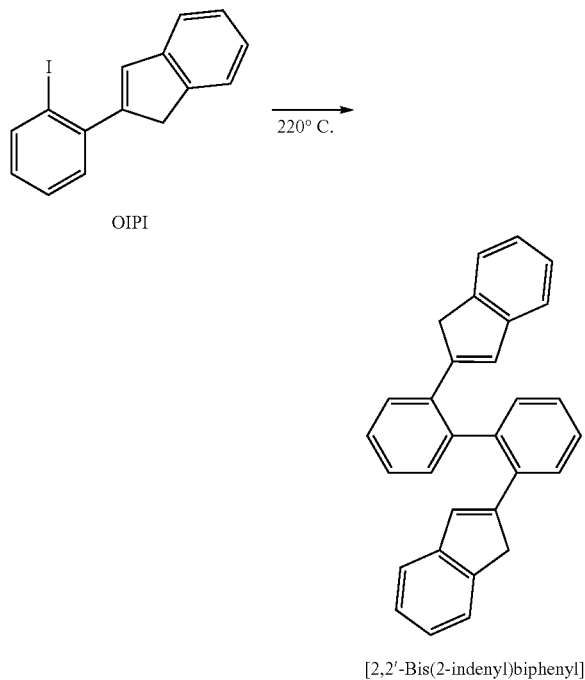

OIPI

[2,2'-Bis(2-indenyl)biphenyl]

Procedure:

In a 50 ml sealed tube, OIPI (0.1 g) was added and heated up to 220° c. The reaction was monitored with TLC. After 16 hours, the desired product was formed. Then a sample was submitted for HPLC. The HPLC analysis did however show that only 5% product was formed.

The comparative experiments above show that coupling of OBPI and OIPI leads to a poor yield for the desired product as well as to the formation of other compounds (impurities).

EXAMPLES ACCORDING TO THE PRESENT INVENTION

Example 1. Preparation of the Compound of Formula (1), Wherein R$^1$, R$^2$, R$^3$, R$^4$, R$^5$, R$^6$, R$^7$, R$^8$, R$^9$, R$^{10}$, R$^{11}$ and R$^{12}$ all Stand for H; Method 1

Synthesis of the Compound of Formula (6):

The compound of formula (7) (10 g, 49.79 mmol), 1,8-diamino naphthalene (8.66 g, 57.77 mmol) and Toluene (200 ml) were charged into a 500 ml four neck round bottom flask. The resulting solution was refluxed overnight and then checked with thin layer chromatography (TLC). The TLC showed that the reaction was complete. After this, the reaction was cooled to room temperature, water (50 ml) was added and the layers were separated. The organic layer was washed with dilute H$_2$SO$_4$ (10%, 50 ml) and the resulting layers were separated. Again the organic layer was washed with saturated sodium chloride solution (100 ml), the layers were separated after which the organic layer was dried over sodium sulphate and the solvent was removed by using Rota evaporator, residue crystallized in Hexane.

Wt.: 10.05 g (HPLC: 99.10%), Yield: 63%

Synthesis of the Compound of Formula (4):

The above synthesized compound-3 (10.05 g, 31.11 mmol), 2-indenyl boronic acid (5.97 g, 37.33 mmol), Tetra butyl ammonium hydroxide (1M in methanol, 94.5 ml, 37.33 mmol) [Pd(PPh$_3$)$_4$](approx 300 mg) and Toluene (100 ml) were charged into a 500 ml four neck flask. The resulting solution was heated to reflux (77-78° C.) for 4 hrs. and then checked with TLC. TLC showed a completion of the reaction, so the reaction was cooled to 5° C. and dilute HCL (10%, 75 ml) and Dichloromethane (100 ml) were added. The obtained layers were separated and the organic layer was washed with saturated sodium chloride. Subsequently, the organic layer was dried over sodium sulphate and the remaining solvent was removed by Rota evaporator and the residue crystallized in Hexane.

Wt.: 6.432 g (HPLC: 86.55%), Yield: 60.6%

Synthesis of the Compound of Formula (1):

The above synthesized compound of formula (4) (6.432 g, 17.95 mmol) and THF (65 ml) were charged into a 250 ml four neck flask, stirring started. Into the resulting solution, dilute H$_2$SO$_4$ (1 M, 20 ml) was slowly added. During addition, the temperature was raised from 15° C. to 25° C. After the addition, the reaction was stirred for 1 hr and then checked with TLC. TLC showed a completion of the reaction, so into the resulting solution Dichloromethane (50 ml) was added. The obtained layers were separated, after which the organic layer was washed with saturated sodium chloride solution, the solvent was distilled out by Rota evaporator and the residue was crystallized in Hexane.

Wt.: 3.216 g (HPLC: 90%), Yield: 76%

The process of this example 1 is also illustrated by the below Scheme 1.

In Scheme 1, a compound of formula (7), wherein X$^3$ stands for Br, wherein R$^9$, R$^{10}$, R$^{11}$, R$^{12}$, R$^{15}$ and R$^{16}$ all stand for H is protected with PG-L (1,8,-diamino naphthalene) to form the corresponding compound of formula (6). The compound of formula (6) is then reacted with the compound of formula (5), wherein R$^1$, R$^2$, R$^3$, R$^4$, R$^5$, R$^6$, R$^{13}$ and R$^{14}$ all stand for H, in a solvent (toluene) in the presence of the Pd catalyst (Pd(PPh$_3$)$_4$) and the base tetra-butylammonium hydroxide to form the corresponding compound of formula (4) after which the compound of formula (4) is deprotected by reaction of the compound of formula (4) with the mild sulphuric acid to form the corresponding compound of formula (1)

Scheme 1.

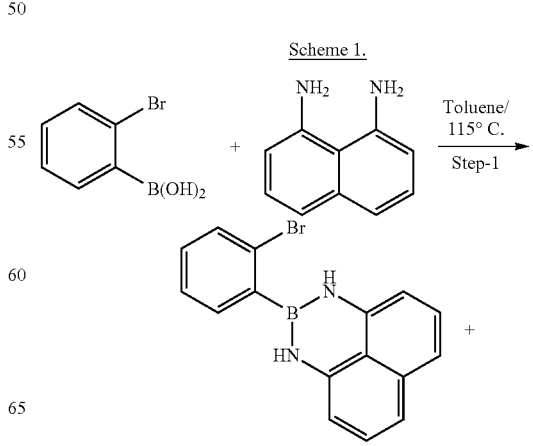

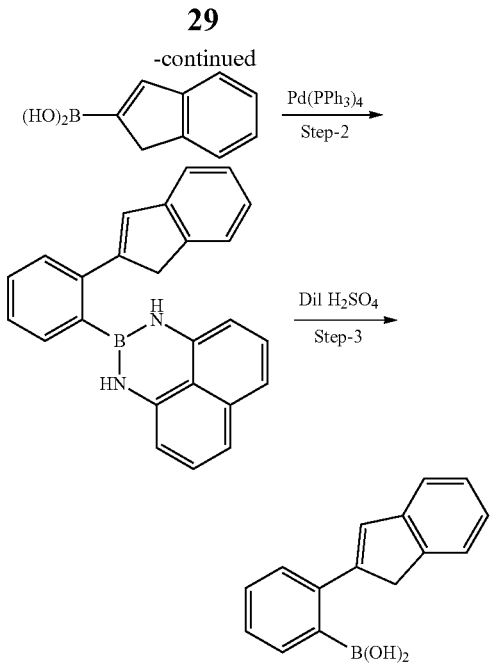

Example 2. Preparation of the Compound of Formula (1), wherein $R^1$, $R^2$, $R^3$, $R^4$, $R^5$, $R^6$, $R^7$, $R^8$, $R^9$, $R^{10}$, $R^{11}$ and $R^{12}$ all Stand for H; Method 2

In a 50 ml four neck flask the following components were charged Mg turning (0.224 g, 9.22 mmol), tetrahydrofuran (THF) (15 ml), Tri methyl borate (3.04 g, 11.07 mmol), Ortho-Bromo-(2-indenyl)Benzene (OBPI) (1 g, 3.69 mmol) and 1, 2-Dibromo ethane (2-3 drops). The resulting solution was heated up to 35° C. and maintained at this temperature for 1 hr. Then it was checked with TLC. TLC showed complete consumption of starting material. Therefore, the heating was stopped, the reaction was cooled down to room temperature, the solution poured into dilute HCL (5%, 25 ml), Dichloromethane (25 ml) was added. The resulting mixture was stirred for 10 minutes and the formed layers were separated. The organic layer was dried over sodium sulphate and the solvent recovered by Rota evaporator. The residue was washed with Hexane (25 ml) to remove Phenyl indene.
Wt.: 250 mg (HPLC: 91%), Yield: 28.7%

The process of example 2 is also illustrated by the process in scheme 2.

Scheme 2

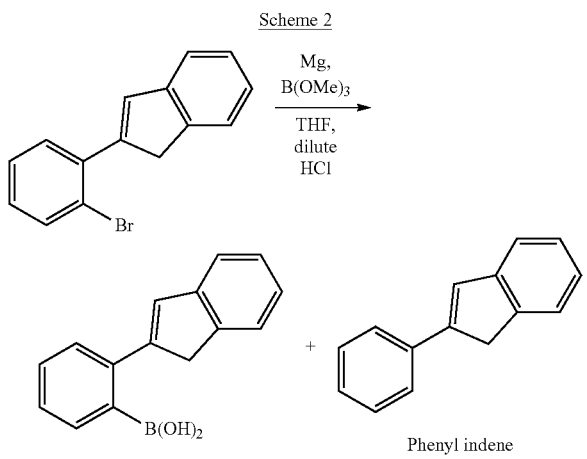

Phenyl indene

In Scheme 2, a compound of formula (9), wherein $R^1$, $R^2$, $R^3$, $R^4$, $R^5$, $R^6$, $R^9$, $R^{10}$, $R^{11}$, $R^{12}$ all stand for H and wherein $X^4$ stands for Br is reacted with the compound of formula (10), wherein $R^{17}$ stands for H in the presence of magnesium and an acid to form the corresponding compound of formula (1).

Example 3. Preparation of 2,2'-bis(2-indenyl) biphenyl

The compound of formula (1), wherein $R^1$, $R^2$, $R^3$, $R^4$, $R^5$, $R^6$, $R^7$, $R^8$, $R^9$, $R^{10}$, $R^{11}$ and $R^{12}$ all stand for H (1 g, 4.2 mmol), Tetra butyl ammonium hydroxide (1M solution in methanol, 5.5 ml, 5.5 mmol), the compound of formula (2), wherein $R^1$, $R^2$, $R^3$, $R^4$, $R^5$, $R^6$, $R^7$, $R^{10}$, $R^{11}$ and $R^{12}$ all stand for H and wherein $X^5$ stands for Br (1.37 g, 5.1 mmol), Pd(PPh$_3$)$_4$ (catalyst, 90 mg) and 15 ml of toluene were charged in 50 ml four neck round bottom flask. Resulted solution was refluxed (77-78° C.) for 1 hrs. and the product immediately started to precipitate out. Reflux continued further 1 hrs. and then checked TLC, it was showing completion of reaction. So the reaction was cooled to 0-5° C., HCl (10%, 10 ml) was added, stirred for 5 minutes, the solution was filtered, residue was washed with water and dried in an oven, to obtain 1.31 g (97% purity by HPLC, 82% yield). However, instead of Pd(PPh$_3$)$_4$, Pd/C may also be employed.

The process of example 3 is also illustrated by Scheme 3 below:

Scheme 3.

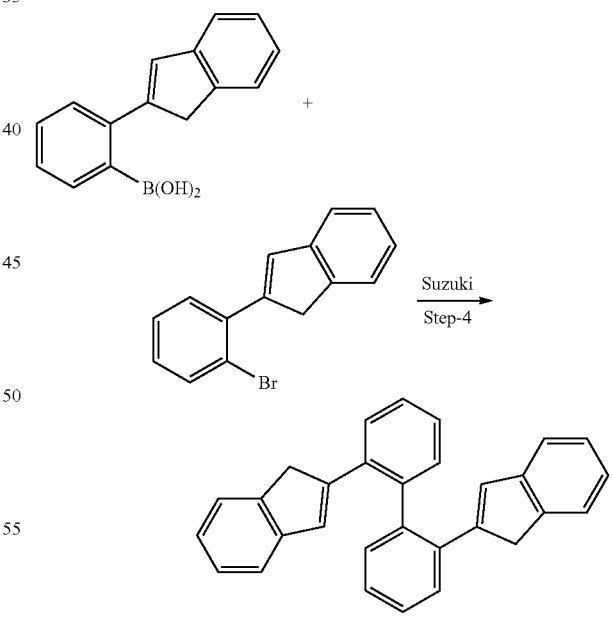

In Scheme 3, a compound of formula (1) (2-boronic acid phenyl indene), wherein $R^1$, $R^2$, $R^3$, $R^4$, $R^5$, $R^6$, $R^7$, $R^8$, $R^9$, $R^{10}$, $R^{11}$ and $R^{12}$ all stand for H and a compound of formula (2) (2-bromo phenyl indene), wherein $R^1$, $R^2$, $R^3$, $R^4$, $R^5$, $R^6$, $R^7$, $R^{10}$, $R^{11}$ and $R^{12}$ all stand for H and wherein $X^5$ stands for Br are reacted in the presence of a Pd catalyst and a base to form the corresponding compound of formula (3).

Example 4. Preparation of the Compound of Formula (1), Wherein $R^1$, $R^2$, $R^3$, $R^4$, $R^5$, $R^6$, $R^9$, $R^{10}$, $R^{11}$ and $R^{12}$ all Stand for H and Wherein $R^7$ and $R^8$ Form a Pinacolyl Ring Together with the Oxygen Atoms to which they are Bound (=Building Block X)

Step 1: 2-indenyl boronic acid (10 g, 56.7 mmol), and 1-bromo-2-chlorobenzene (13.03 g, 68.01 mmol), Tetra butyl ammonium hydroxide (1M in Methanol, 68 ml, 68.04 mmol), Tetrakis palladium triphenyl phosphine (400 mg) and Toluene (100 ml) charged in to 500 ml four neck flask. Resulted solution was heated to reflux (78° C.-80° C.) and reflux continued for further 5 hrs. Then sample submitted for HPLC, it was showing completion of reaction. So heating stopped, reaction cooled down 5° C. temperature. Then added dilute HCL (10%, 75 ml), stirred for 10 minutes, separated layers, organic layer washed with dilute sodium chloride solution and dried over Sodium sulphate. Solvent removed by Rota evaporator to afford the crude product, 2-chloro phenylindene (14.2 g, purity by HPLC 85%). Thereafter, crude 2-chloro phenyl indene was purified by high vacuum distillation. (Vapor temperature: 165-175° C., Vacuum: 0.7-0.8 mbar). After high vacuum distillation: Weight=10 g (HPLC=96.6%), Yield: 73.7%

Above synthesized compound, 2-chloro phenylindene (5 g, 22.05 mmol), bis-pinacolato diboron (6.44 g, 25.36 mmol), triethyl amine (5.56 g, 55 mmol), Ni(COD)$_2$ (217 mg), triphenyl phosphine (415 mg) and Methanol (50 ml) was charged in to 100 ml RB flask. Resulted solution was heated to reflux (55° C.-57° C.) for an overnight. Then reaction was cooled to 10° C. and added dilute HCl (40 ml). Then added Dichloromethane (50 ml, Ethyl acetate also can be used), separated layers, organic layer washed with saturated sodium chloride solution. Solvents removed by Rota evaporator. Wt. of crude building block X (8.0 g).

The process of example 4 is illustrated by the below Scheme 4:

In Scheme 4, a compound of formula (12X), wherein $R^9$, $R^{10}$, $R^{11}$ and $R^{12}$ all stand for H and wherein $X^1$ stands for Br and wherein $X^2$ stands for Cl is reacted with a compound of formula 5, wherein $R^1$, $R^2$, $R^3$, $R^4$, $R^5$, $R^6$, $R^{13}$ and $R^{14}$ all stand for H in a solvent (toluene) in the presence of a Pd catalyst (Pd(PPh$_3$)$_4$) and a base (TBAOH=Tetra butyl ammonium hydroxide) to form the corresponding compound of formula (13) and reacting the compound of formula (13) with the compound of formula 14X in a solvent, in the presence of Ni(COD)$_2$, triphenylphosphine and a base to form the corresponding compound of formula (1X) (also referred to herein as building block X).

Scheme 4.

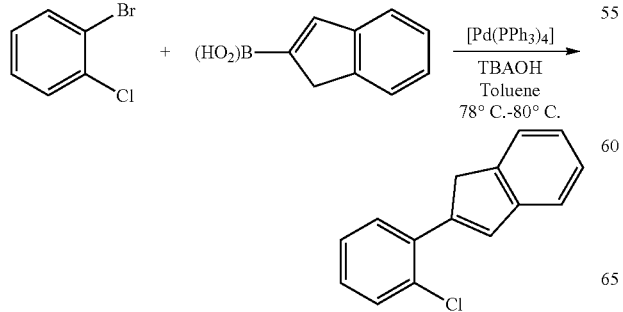

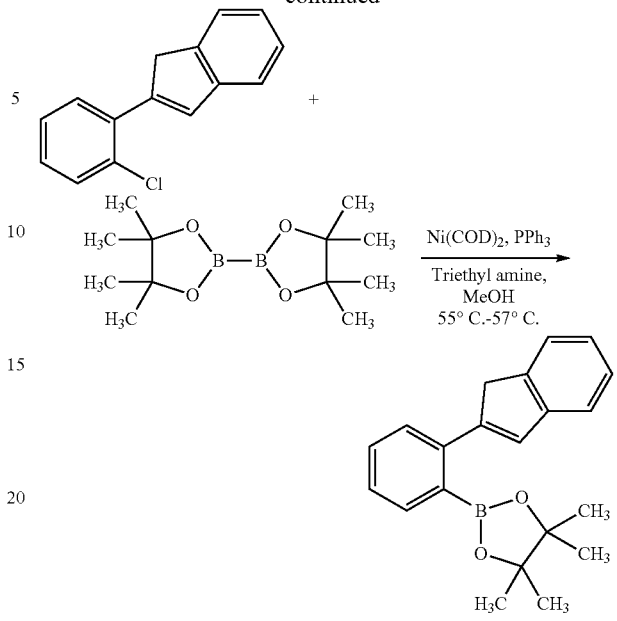

Example 5. Preparation of Bis(2-Indenyl) Biphenyl from Building Block X

Building block X (8.0 g), building block Y, tetra butyl ammonium hydroxide (25.13 ml, 1M solution in methanol), tetrakis palladiumtriphenyl phosphine (200 mg) and toluene (120 ml) were added into a roundbottom flask and the resulting solution was heated to reflux (78° C.-80° C.) and the product immediately started to precipitate out and heating was continued for 3 hours. Then TLC was used and it showed completion of the reaction. Then the reaction was cooled down to 10° C., dilute HCl (50 ml) was added, stirred for 10 minutes and the solution was filtered off, the residue was washed with water and methanol and dried in an oven to afford 3 g of product. (2,2'-bi(2-indenyl)biphenyl).

The process of example 5 is illustrated by the below Scheme 5:

Scheme 5.

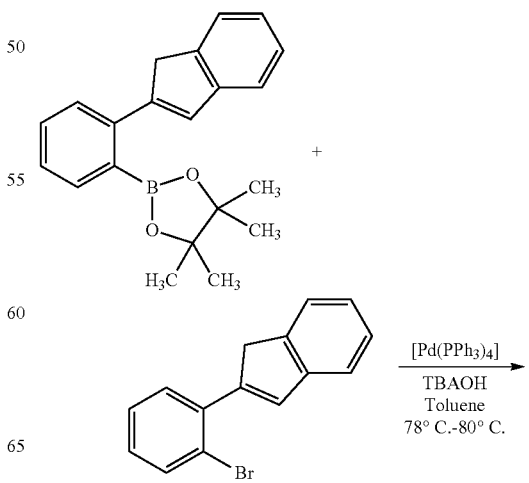

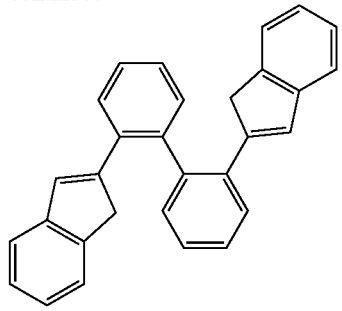

In Scheme 5, the compound of formula (1), wherein $R^1$, $R^2$, $R^3$, $R^4$, $R^5$, $R^6$, $R^9$, $R^{10}$, $R^{11}$ and $R^{12}$ all stand for H and wherein $R^7$ and $R^8$ together with the oxygen atoms to which they are bound for a pinacolyl ring (building block X) is reacted with the compound of formula (2), wherein $R^1$, $R^2$, $R^3$, $R^4$, $R^5$, $R^6$, $R^9$, $R^{10}$, $R^{11}$ and $R^{12}$ all stand for H and wherein $X^5$ stands for Br (building block Y) in a solvent in the presence of a Pd catalyst ($Pd(PPh_3)_4$) and a base.

2,2'-bis(2-indenyl)biphenyl]zirconiumdichloride 2,2'-bis(2-indenyl) biphenyl]zirconiumdichloride (the compound of formula (15), wherein $R^1$, $R^2$ $R^1$, $R^2$, $R^3$, $R^4$, $R^5$, $R^6$, $R^9$, $R^{10}$, $R^{11}$ and $R^{12}$ all stand for H, wherein M stands for Zr and wherein Q stands for Cl and wherein k stands for 2 can be prepared from 2,2'-bis(2-indenyl)biphenyl (the compound of formula (3), wherein ($R^1$, $R^2$ $R^1$, $R^2$, $R^3$, $R^4$, $R^5$, $R^6$, $R^9$, $R^{10}$, $R^{11}$ and $R^{12}$ all stand for H) as described in EP1059300A1, example VIII.4, [0106] and [107]:

"A 100 cc Schlenk charged with a stirring bar and 2,2'-bis(2-indenyl)biphenyl (3.84 g, 10.0 mmol) was brought under an atmosphere of dry. Dry ether (40 mL) was added. The resulting suspension was cooled to 0° C. by ice-bath, and a solution of n-butyllithium (1.6 M in hexanes, 12.5 mL, 20.0 mmol) was added. The mixture was allowed to warm to room temperature. slowly. The crystals slowly dissolved, while a fine suspension formed. Stirring at room temperature was continued for 4 hour.

Meanwhile, a suspension of zirconium tetrachloride (2.34 g, 10 mmol) in dry ether (40 mL) was prepared. The suspensions (of dianion in ether and of zirconium tetrachloride in ether) were cooled in an acetone/dry ice bath, and mixed via a bended connection tube. The temperature was allowed to rise to room temperature. After stirring for two days, the suspension was filtered (under nitrogen atmosphere), and the residue washed with dry ether three times (the last washing was colourless). The residue was dissolved partly in boiling toluene (260 mL), and the suspension filtered hot under an atmosphere of dry nitrogen The clear yellow filtrate was cooled slowly to ambient temperature, giving yellow crystals of pure product (3.30 g, 6.08 mmol, 60.6%). The filtrate was used to extract the residue once more (boiling), and cooling to −20 DEG C. afforded another crop (0.65 g, 1.2 mmol, 12%)."

2,2'-bis(2-indenyl) biphenyl zirconiumdichloride can then be placed on a support as described in EP1059300A1, paragraphs [0109] and [0110]:

"Supported 2,2'-bis(2-indenyl)biphenyl zirconiumdichloride

Silica (Grace Davison 2101) was heated at 200° C. under a stream of nitrogen for 6 hours. To 7.3 g of this silica was added 70 ml of toluene. The slurry was stirred and 49.4 ml of a 10 wt-% of methylalumoxane (diluted from a 30 wt % solution in toluene obtained from Albemarle) was added slowly. The resulting slurry was stirred for 16 hours at room temperature (20° C.), after which the solvent was removed by evaporation at 30° C.

To a slurry of 2.1 g of the obtained solid in 30 ml of toluene was added a solution of 24 mg of [2,2'-bis(2-indenyl)biphenyl]-zirconiumdichloride in 20 mL of toluene, and the resulting slurry was stirred overnight. The slurry was then decanted and dried by evaporation at 35° C."

An improved way of preparing the supported 2,2'-bis(2-indenyl)biphenyl zirconiumdichloride from diphenyl(2-indenyl)$_2$ZrCl$_2$ is described in WO 2013/097936A1, example 9:

Example 9. Large Scale Preparation of the Catalyst Composition of the Invention

At room temperature, 0.595 kg of diphenyl(2-indenyl)$_2$ZrCl$_2$ was added to 36.968 kg of a 30% methylaluminoxane solution (Al content 13.58 wt %) and stirred for 30 minutes to form activated metallocene. About 172 kg of dry toluene was added to 43 kg of silica 955 to form a silica slurry. At about 30° C., the activated metallocene was added to the silica slurry under agitation. After the activated metallocene was added, the temperature was increased to 50° C. After 2 hours at 50° C., all of modifier F (wherein modifier F was prepared by, at room temperature, slowly adding 0.114 kg of neat triisobutylaluminum to a solution of 0.059 of cyclohexylamine in 9.7 kg of dry toluene) was added. After addition the mixture was kept at 50° C. for 1 hour. The reaction temperature was then reduced to 30° C. The toluene was removed by filtration and the obtained catalysts composition was dried by raising the temperature to 55° C. and using a flow of warm nitrogen. The Al/Zr ratio used in this experiment was approximately 150."

The supported 2,2'-bis(2-indenyl)biphenyl zirconiumdichloride can then be used in a polymerization, for example as described in WO2013/097936A1 or for example as described in EP1059300A1, examples X-IX:

"400 ml of pentamethyl heptane (abbreviation: PMH), ethylene and, eventually, 25 ml 1-octene were supplied to a 1.3-liter reactor, with heating to polymerisation temperature (Tp); the pressure was 2 MPa. Next, 0.78 ml (1.6 M solution in toluene) of methylaluminoxane (Witco) and the catalyst solution or slurry (0.125 ml of a 0.001 m solution in toluene) were premixed at room temperature for 1 minute and then supplied to the reactor. The catalyst supply vessel was rinsed out with 100 ml of pentamethylheptane (PMH). The pressure in the reactor was kept constant by supplying ethene. By cooling the reactor the temperature deviation from the setting was limited to a maximum of 5° C. After 10 minutes the polymerisation was stopped and the polymer was worked up by draining the solution and boiling it down under vacuum at 50° C.".

The invention claimed is:
1. A process comprising
reacting a compound of formula (1)

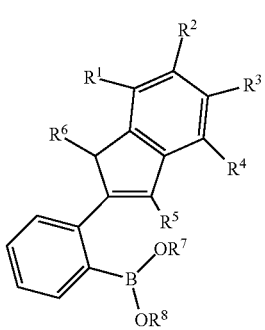

(1)

wherein $R^1$, $R^2$, $R^3$, $R^4$, $R^5$ and $R^6$ each independently stand for H or a hydrocarbon radical having 1-20 C-atoms, and wherein $R^7$ and $R^8$ each independently stand for H, or an alkyl or aryl or wherein $R^7$ and $R^8$ optionally form a ring together with the oxygen atoms to which they are bound, with a compound of formula (2)

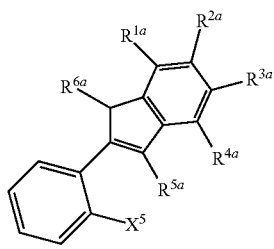

(2)

wherein $R^{1a}$, $R^{2a}$, $R^{3a}$, $R^{4a}$, $R^{5a}$, and $R^{6a}$ each independently stand for H or a hydrocarbon radical having 1-20 C-atoms, and wherein $X^5$ stands for a halogen in a solvent in the presence of a Pd catalyst and a base, to form the corresponding compound of formula (3)

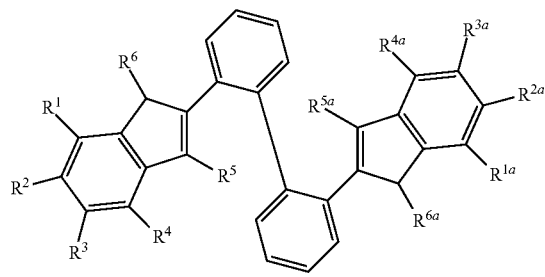

(3)

wherein, in formula (3), $R^1$, $R^2$, $R^3$, $R^4$, $R^5$, $R^{1a}$, $R^{2a}$, $R^{3a}$, $R^{4a}$, $R^{5a}$, and $R^{6a}$ are as defined in formula (1) and formula (2), respectively, wherein the solvent is an aromatic solvent, an ether solvent, an alcohol solvent, water, or a combination comprising at least one of the foregoing, wherein the Pd catalyst is a Pd(0) catalyst, and wherein the base is a quaternary ammonium salt, a tertiary amine, or an alkali or alkaline earth metal salt of acetate, alkoxide, carbonate, halide, hydroxide, or phosphate.

2. The process according to claim 1, wherein $R^1$, $R^2$, $R^3$, $R^4$, $R^5$, $R^6$, $R^{1a}$, $R^{2a}$, $R^{3a}$, $R^{4a}$, $R^{5a}$, $R^{6a}$ are hydrogen.

3. The process according to claim 1, wherein $R^7$ and $R^8$ are hydrogen.

4. The process according to claim 1, wherein $R^7$ and $R^8$ form a pinacolyl ring together with the oxygen atoms to which they are bound.

5. The process according to claim 1, wherein $X^5$ is Cl or Br.

6. The process according to claim 1, wherein the Pd catalyst is tetrakis(triphenylphosphine) palladium (0), tris (dibenzylideneacetone) dipalladium(0), bis(tricyclohexylphosphine) palladium(0), bis(tri-t-butylphosphine) palladium(0), bis[1.2-bis(diphenylphosphino)ethane] palladium (0), or palladium on carbon.

7. The process according to claim 1, wherein the Pd catalyst is $Pd(PPh_3)_4$.

8. The process according to claim 1, wherein the solvent is methanol, ethanol, benzene, toluene, xylene, tetrahydrofuran, dioxane, dimethoxyethane, water, or a combination comprising at least one of the foregoing.

9. The process according to claim 1, wherein the solvent is toluene.

10. The process according to claim 1, wherein the base is tetrabutylammonium hydroxide, tetra n-butylammonium acetate, triethylamine, sodium carbonate, sodium acetate, sodium tert-butoxide, potassium carbonate, potassium iodide, sodium iodide, potassium acetate, cesium carbonate, cesium fluoride, lithium hydroxide, sodium hydroxide, sodium ethoxide, potassium fluoride, or potassium phosphate.

* * * * *